US008206723B2

(12) United States Patent
Steward et al.

(10) Patent No.: US 8,206,723 B2
(45) Date of Patent: Jun. 26, 2012

(54) LEUCINE-BASED MOTIF AND CLOSTRIDIAL NEUROTOXINS

(75) Inventors: Lance E. Steward, Irvine, CA (US); Ester Fernandez-Salas, Fullerton, CA (US); Todd M. Herrington, Brookline, MA (US); Kei Roger Aoki, Coto De Caza, CA (US)

(73) Assignee: Allergan, Inc., Irvine, CA (US)

( * ) Notice: Subject to any disclaimer, the term of this patent is extended or adjusted under 35 U.S.C. 154(b) by 314 days.

(21) Appl. No.: 12/416,470

(22) Filed: Apr. 1, 2009

(65) Prior Publication Data
US 2009/0202591 A1 Aug. 13, 2009

Related U.S. Application Data

(60) Continuation of application No. 10/753,537, filed on Jan. 8, 2004, now Pat. No. 7,534,863, and a division of application No. 09/910,346, filed on Jul. 20, 2001, now abandoned, and a continuation-in-part of application No. 09/620,840, filed on Jul. 21, 2000, now Pat. No. 6,903,187.

(51) Int. Cl.
*C07K 14/33* (2006.01)
(52) U.S. Cl. .................................... 424/239.1; 530/350
(58) Field of Classification Search .................. None
See application file for complete search history.

(56) References Cited

U.S. PATENT DOCUMENTS

| 4,932,936 | A | 6/1990 | Dykstra et al. |
| 5,053,005 | A | 10/1991 | Borodic |
| 5,437,291 | A | 8/1995 | Pasricha et al. |
| 5,670,484 | A | 9/1997 | Binder |
| 5,714,468 | A | 2/1998 | Dao |
| 5,721,215 | A | 2/1998 | Aoki et al. |
| 5,766,605 | A | 6/1998 | Sanders et al. |
| 5,939,070 | A | 8/1999 | Johnson et al. |
| 5,989,545 | A | 11/1999 | Foster et al. |
| 6,063,768 | A | 5/2000 | First |
| 6,113,915 | A | 9/2000 | Aoki et al. |
| 6,139,845 | A | 10/2000 | Donovan |
| 6,143,306 | A | 11/2000 | Donovan |
| 6,265,379 | B1 | 7/2001 | Donovan |
| 6,299,893 | B1 | 10/2001 | Schwartz et al. |
| 6,306,403 | B1 | 10/2001 | Donovan |
| 6,306,423 | B1 | 10/2001 | Donovan |
| 6,312,708 | B1 | 11/2001 | Donovan |
| 6,328,977 | B1 | 12/2001 | Donovan |
| 6,358,513 | B1 | 3/2002 | Voet et al. |
| 6,365,164 | B1 | 4/2002 | Schmidt |
| 6,395,277 | B1 | 5/2002 | Graham |
| 6,423,319 | B1 | 7/2002 | Brooks et al. |
| 6,458,365 | B1 | 10/2002 | Aoki et al. |
| 6,464,986 | B1 | 10/2002 | Aoki et al. |

FOREIGN PATENT DOCUMENTS

| WO | WO 94/15629 | 7/1994 |
| WO | WO 96/39166 | 12/1996 |
| WO | WO 97/32599 | 9/1997 |
| WO | WO 00/05252 | 2/2000 |

OTHER PUBLICATIONS

Zhou et al in Biochemistry 34: 15175-15181, 1995.
Aoki in "Toxicon", 12: 1815-1820, 2001.
Darsow et al in "J. Cell Biol." 142: 913-922, 1998.
Rudinger, In "Peptide Hormones" (ed. J.A. Parsons), University Park Press, Baltimore, pp. 1-7 (1976).
Elston et al in "Br. J. Ophthalmol", 69: 891-896, 1985.
Kadkhodayan et al, "Protein Express. Purif."; 19: 125-130, 2000.
Lacy et al, "Nat. Struct. Biol.", 5: 898-902, 1998.
Peden et al, J. Biol. Chem. 276: 49183-49187, 2001.
Arnon, et al., "Botulinum toxin as a biological weapon: medical and public health management," JAMA (2001) 285:1059-1070.
Eswaramoorthy, et al., "A novel mechanism for *Clostridium botulinum* neurotoxin inhibition, " Biochemistry (2002) 41:9795-9802.
Aoki, et al., "Is the light chain subcellular localization an important factor for Botulinum neurotoxin duration of action?," Naunyn Schmiedebergs Arch. Pharmacol. (2002) 365 (Suppl 2):R10.
Fernandez-Salas, et al., "Localization of BoNT light chains in neuronal and non-neuronal cell lines, implications for the duration of action of the different serotypes," Naunyn Schmiedebergs Arch. Pharmacol. (2002) 365 (Suppl 2):R19.
Steward, et al., "BoNT/A light chain and the dileucine motif: potential implications for light chain localization and neurotoxin duration of action," Naunyn Schmiedebergs Arch. Pharmacol. (2002) 365 (Suppl 2):R44.
Fernandez-Salas, et al., "Plasma Membrane Localization Signals in the Light Chain of Botulinum Neurotoxin," Slide presentation at USAMRDD, Jan. 2004.
Fernandez-Salas, et al., "Plasma membrane localization signals in the Light chain of botulinum neurotoxin," Proc. Natl. Acad. Sci. USA (2004) 101:3208-3213.
Fernandez-Salas, et al., "Is the light chain subcellular localization an important factor in Botulinum toxin duration of action?" Movement Disorders (2004) 19:S23-S34.
Shin et al, "Phosphorylation-Dependent Down-Modulation . . . " Journal of Biological Chemistry 266: 10658-10665, 1991.
Raciborska & Charlton, "Retention of Cleaved Synaptosome-Associated . . . " Can J. Physiol, 77: 679-688, 1999.

(Continued)

*Primary Examiner* — Robert C Hayes
(74) *Attorney, Agent, or Firm* — Kenton Abel; Debra Condino

(57) ABSTRACT

Modified neurotoxin comprising neurotoxin including structural modification, wherein the structural modification alters the biological persistence, such as the biological half-life and/or a biological activity of the modified neurotoxin relative to an identical neurotoxin without the structural modification. In one embodiment, methods of making the modified neurotoxin include using recombinant techniques. In another embodiment, methods of using the modified neurotoxin to treat conditions include treating various disorders, neuromuscular aliments and pain.

4 Claims, 10 Drawing Sheets

OTHER PUBLICATIONS

Erdal et al, "Processing of Tetanus and Botulinum A . . . " Naunyn-Schmiedeberg's Arch Pharmacol 351: 67-78, 1995.
Ragona et al, "Management of Parotid Sialocele . . . " The Laryngoscope 109: 1344-1346, 1999.
Naumann et al, Botulinum Toxin Type A in the Treatment . . . European Journal of Neurology 6: S111-S115, 1999.
Keller et al, "Persistence of Botulinum Neurotoxin . . . " Federation of European Biochemical Societies Letters 456: 137-142, 1999.
Dietrich et al, "Regulation and Function of the CD3yDxxxLL Motif . . . " Journal of Cell Biology 138: 271-281, 1997.
Geisler et al, "Leucine-Based Receptor Sorting Motifs . . . " journal of Biological Chemistry 273: 21316-21323, 1998.
Tan et al, "A Leucine-Based Motif Mediates the Endocytosis . . . " Journal of Biological Chemistry 273: 17351-17360, 1998.
Liu et al, "Membrane Trafficking of Neurotransmitter . . . " Trends in Cell Biology 9:356-363, 1999.
Cai & Singh, Biochemistry, vol. 40, 2001, p. 4693.
Tikkanen et al, Traffic, vol. 1, 2000, pp. 631-640.
Rapaport et al, The Embo Journal, vol. 17, No. 8, 1998, pp. 2148-2155.
Miranda et al, JBC Papers in Press, 2001, pp. 1-35.
Cowles et al, Cell, vol. 91, 1997, pp. 109-118.
Aoki, J. Neurol, vol. 248 (Supp. 1), 2001, pp. 3-10.
Elston et al, British Journal of Ophthalmology, vol. 69, 1985, pp. 718-724, 891-896.
Adenis et al, J. FR. Ophthalmology, vol. 13, No. 5, 1990, pp. 259-264.
Jankovic et al, Neurology, vol. 37, 1987, pp. 616-623.
Blitzer et al, Ann. Otol. Rhino. Laryngol, vol. 94, 1985, pp. 591-594.
Brin et al, Advanced Neurology, vol. 50, pp. 599-608.
Cohen et al, Neurology, vol. 37, (Supp. 1) 1987, pp. 123-124.
Galli et al, Mol. Biol. Cell, vol. 9, 1998, pp. 1437-1438.
Martinez-Arca et al, J. Cell Biol., vol. 149, 2000, pp. 889-899.
Weigand et al, Nauny Schmiedeberg's Arch. Pharmocology, vol. 292, 1976.
Haberman, Nauny Schmeideberg's Arch. Pharmacology, vol. 281, 1974.
Li et al, Biochemistry, vol. 33, 1994, pp. 7014-7020.
Zhou et al, Biochemistry, vol. 34, 1995, pp. 15, 175-15, 181.
Binz et al, J. Biol. Chem., vol. 265 1990, p. 9153.
Thompson et al, Eur. J. Biochem., vol. 189, 1990, p. 73.
Minton, Clostridial Neurotoxins, The Molecular Pathogenesis of Tetanus and Botulism, Edited by Motecucco, 1995, pp. 161-191.
Di Bello et al, Eur. J. Biochem., vol. 219, 1993, p. 161.
Kozaki et al, Japan J. Med. Sci. Biol., vol. 34, 1981, p. 61.
Maisey et al, Eur. J. Biochem., vol. 177, 1988, p. 683.
Milton et al, Biochemistry, vol. 31, 1992, pp. 8799-8809.
Swain et al, Peptide Research, vol. 6, 1993, pp. 147-154.

FIG. 3.

```
      ΔN8
      ─────────
  1   PFVNKQFNYKDPVNGVDIAYIKIPNAGQMQPVKAFKIHNKIWVIPERDTF
 51   TNPEEGDLNPPPEAKQVPVSYYDSTYLSTDNEKDNYLKGVTKLFERIYST
101   DLGRMLLTSIVRGIPFWGGSTIDTELKVIDTNCINVIQPDGSYRSEELNL
151   VIIGPSADIIQFECKSFGHEVLNLTRNGYGSTQYIRFSPDFTFGFEESLE
201   VDTNPLLGAKFATDPAVTLAHELIHAGHRLYGIAINPNRVFKVNTNAYY
251   EMSGLEVSFEELRTFGGHDAKFIDSLQENEEFRLYYNKFKDIASTLNKAK
301   SIVGTTASLQYMKNVFKEKYLLSEDTSGKFSVDKLKFDKLYKMLTEIYTE
351   DNFVKFFKVLNRKTYLNFDKAVFKINIVPKVNYTIYDGENLRNTNLAANF
                                   ΔC22
                              ──────────────────────
401   NGQNTEINNMNFTKLKNFTGLFEFYKLLCVRGIITSK
                                   ══════════════════
```

FIG. 8.

```
                       1                                                                         75
BoNT/A (Hall A) LC     -PFVNKQFNYKDPVNGVDIAYIKIPNAGQMQPV-KAFKIHNKIWVIPERDTFTNPEEGDLNPPPEAKQVPVSYYD
BoNT/B (Danish I) LC   MPVTINNFNYNDPIDNNNIIMMEPPFARGTGRYYKAFKITDRIWIIPERYTFGYKPEDFNKSSGIFNRDVCEYYD
                        P    NFNY DPI    I  I P        KAFKI  KIWIIPER TF    E                  YYD 76                                                                       150
BoNT/A (Hall A) LC     STYLSTDNEKDNYLKGVTKLFERIYSTDLGRMLLTSIVRGIPFWGGSTIDTELKVIDTNCINVIQPDGSYR-SEE
BoNT/B (Danish I) LC   PDYLNTNDKKNIFLQTMIKLFNRIKSKPLGEKLLEMIINGIPYLGDRRVPLEEFNTNIASVTVNKLISNPGEVER
                         YL T   K  FL  M KLF RI S  LG  LL  II GIPF G   I E        I V          E 151                                                                      225
BoNT/A (Hall A) LC     -----LNLVIIGPSADIIQFECKSFGHEVLNLTRNGYGSTQYIRFSPDFTFGFEESLEVDTNPLLGAGKFATDPA
BoNT/B (Danish I) LC   KKGIFANLIIFGPGPVLNENETIDIGIQNHFASREGFGGIMQMKFCPEYVSVFNNVQENKGASIFNRRGYFSDPA
                             NLII GP   I  E    G      SR GFG    IKF PDF   F    E     I     F SDPA 226                                                                      300
BoNT/A (Hall A) LC     VTLAHELIHAGHRLYGIAINPNRVFKVNTNAYYEMSGLEVSFEELRTFGGHDAKFIDSLQENEFRLYYYNKFKDI
BoNT/B (Danish I) LC   LILMHELIHVLHGLYGIKVD-DLPIVPNEKKFFMQSTDAIQAEELYTFGGQDPSIITPSTDKSIYDKVLQNFRGI
                       L L HELIH  H LYGI I          N    FF  S   I  EEL TFGG D   I   D          N FK I 301                                                                      375
BoNT/A (Hall A) LC     ASTLNKAKSIVG-TTASLQYMKNVFKEKYLLSEDTSGKFSVDKLKFDKLYKMLTEIYTEDNFVKFFKVLNRKTYL
BoNT/B (Danish I) LC   VDRLNKVLVCISDPNININIYKNKFKDKYKFVEDSEGKYSIDVESFDKLYKSLMFGFTETNIAENYKIKTRASYF
                          LNK    I      IN  KN FKDKY    EDS GKFSID    FDKLYK L    FTE N       FKI  R SY 376                                                                447
BoNT/A (Hall A) LC     NFDKAVFKIN-IVPKVNYTIYDGFNLRNTNLAANFNGQNTEINNMNFTKLKNFTGLFEFYKLLCVRGIITSK
BoNT/B (Danish I) LC   SDSLPPVKIKNLLDNEIYTIEEGFNISDKDMEKEYRGQNKAINKQAYEEIS--KEHLAVYKIQMCKSVK---
                              KI  IL     YTI DGFNI      L    F GQN  IN    F  I         YKI   K I
```

LEUCINE-BASED MOTIF AND CLOSTRIDIAL NEUROTOXINS

CROSS REFERENCE

This application is a continuation and claims priority pursuant to 35 U.S.C. §120 to U.S. patent application Ser. No. 10/753,537, filed Jan. 8, 2004, now U.S. Pat. No. 7,534,863 a divisional application that claims priority pursuant to 35 U.S.C. §120 to U.S. patent application Ser. No. 09/910,346, filed Jul. 20, 2001, now abandoned, a continuation-in-part application that claims priority pursuant to 35 U.S.C. §120 to U.S. patent application Ser. No. 09/620,840, filed Jul. 21, 2000, now U.S. Pat. No. 6,903,187 each of which is hereby incorporated by reference in its entirety.

BACKGROUND

The present invention relates to modified neurotoxins, particularly modified Clostridial neurotoxins, and use thereof to treat various conditions including conditions that have been treated using naturally occurring botulinum toxins.

Botulinum toxin, for example, botulinum toxin type A, has been used in the treatment of numerous conditions including pain, skeletal muscle conditions, smooth muscle conditions and glandular conditions. Botulinum toxins are also used for cosmetic purposes.

Numerous examples exist for treatment using botulinum toxin. For examples of treating pain see Aoki, et al., U.S. Pat. No. 6,113,915 and Aoki, et al., U.S. Pat. No. 5,721,215. For an example of treating a neuromuscular disorder, see U.S. Pat. No. 5,053,005, which suggests treating curvature of the juvenile spine, i.e., scoliosis, with an acetylcholine release inhibitor, preferably botulinum toxin A. For the treatment of strabismus with botulinum toxin type A, see Elston, J. S., et al., British Journal of Opthalmology, 1985, 69, 718-724 and 891-896. For the treatment of blepharospasm with botulinum toxin type A, see Adenis, J. P., et al., J. Fr. Opthalmol., 1990, 13 (5) at pages 259-264. For treating spasmodic and oromandibular dystonia torticollis, see Jankovic et al., Neurology, 1987, 37, 616-623. Spasmodic dysphonia has also been treated with botulinum toxin type A. See Blitzer et al., Ann. Otol. Rhino. Laryngol, 1985, 94, 591-594. Lingual dystonia was treated with botulinum toxin type A according to Brin et al., Adv. Neurol. (1987) 50, 599-608. Cohen et al., Neurology (1987) 37 (Suppl. 1), 123-4, discloses the treatment of writer's cramp with botulinum toxin type A.

It would be beneficial to have botulinum toxins with altered biological persistence and/or altered biological activity. For example, a botulinum toxin can be used to immobilize muscles and prevent limb movements after tendon surgery to facilitate recovery. It would be beneficial to have a botulinum toxin (such as a botulinum toxin type A) which exhibits a reduced period of biological persistence so that a patient can regain muscle use and mobility at about the time they recover from surgery. Furthermore, a botulinum toxin with an altered biological activity, such as an enhanced biological activity can have utility as a more efficient toxin (i.e. more potent per unit amount of toxin), so that less toxin can be used.

toxin (i.e. more potent per unit amount of toxin), so that less toxin can be used.

Additionally, there is a need for modified neurotoxins (such as modified Clostridial toxins) which can exhibit an enhanced period of biological persistence and modified neurotoxins (such as modified Clostridial toxins) with reduced biological persistence and/or biological activity and methods for preparing such toxins.

DEFINITIONS

Before proceeding to describe the present invention, the following definitions are provided and apply herein.

"Heavy chain" means the heavy chain of a Clostridial neurotoxin. It has a molecular weight of about 100 kDa and can be referred to herein as Heavy chain or as H.

"$H_N$" means a fragment (having a molecular weight of about 50 kDa) derived from the Heavy chain of a Clostridial neurotoxin which is approximately equivalent to the amino terminal segment of the Heavy chain, or the portion corresponding to that fragment in the intact Heavy chain. It is believed to contain the portion of the natural or wild type Clostridial neurotoxin involved in the translocation of the light chain across an intracellular endosomal membrane.

"$H_C$" means a fragment (about 50 kDa) derived from the Heavy chain of a Clostridial neurotoxin which is approximately equivalent to the carboxyl terminal segment of the Heavy chain, or the portion corresponding to that fragment in the intact Heavy chain. It is believed to be immunogenic and to contain the portion of the natural or wild type Clostridial neurotoxin involved in high affinity binding to various neurons (including motor neurons), and other types of target cells.

"Light chain" means the light chain of a Clostridial neurotoxin. It has a molecular weight of about 50 kDa, and can be referred to as light chain, L or as the proteolytic domain (amino acid sequence) of a Clostridial neurotoxin. The light chain is believed to be effective as an inhibitor of exocytosis, including as an inhibitor of neurotransmitter (i.e. acetylcholine) release when the light chain is present in the cytoplasm of a target cell.

"Neurotoxin" means a molecule that is capable of interfering with the functions of a cell, including a neuron. The "neurotoxin" can be naturally occurring or man-made. The interfered with function can be exocytosis.

"Modified neurotoxin" means a neurotoxin which includes a structural modification. In other words, a "modified neurotoxin" is a neurotoxin which has been modified by a structural modification. The structural modification changes the biological persistence, such as the biological half-life (i.e. the duration of action of the neurotoxin) and/or the biological activity of the modified neurotoxin relative to the neurotoxin from which the modified neurotoxin is made or derived. The modified neurotoxin is structurally different from a naturally existing neurotoxin.

"Mutation" means a structural modification of a naturally occurring protein or nucleic acid sequence. For example, in the case of nucleic acid mutations, a mutation can be a deletion, addition or substitution of one or more nucleotides in the DNA sequence. In the case of a protein sequence mutation, the mutation can be a deletion, addition or substitution of one or more amino acids in a protein sequence. For example, a specific amino acid comprising a protein sequence can be substituted for another amino acid, for example, an amino acid selected from a group which includes the amino acids alanine, aspargine, cysteine, aspartic acid, glutamic acid, phenylalanine, glycine, histidine, isoleucine, lysine, leucine, methionine, proline, glutamine, arginine, serine, threonine, valine, tryptophan, tyrosine or any other natural or non-naturally occurring amino acid or chemically modified amino acids. Mutations to a protein sequence can be the result of mutations to DNA sequences that when transcribed, and the resulting mRNA translated, produce the mutated protein sequence. Mutations to a protein sequence can also be created by fusing a peptide sequence containing the desired mutation to a desired protein sequence.

"Structural modification" means any change to a neurotoxin that makes it physically or chemically different from an identical neurotoxin without the structural modification.

"Biological persistence" or "persistence" means the time duration of interference or influence caused by a neurotoxin or a modified neurotoxin with a cellular (such as a neuronal) function, including the temporal duration of an inhibition of exocytosis (such as exocytosis of neurotransmitter, for example, acetylcholine) from a cell, such as a neuron.

"Biological half-life" or "half-life" means the time that the concentration of a neurotoxin or a modified neurotoxin, preferably the active portion of the neurotoxin or modified neurotoxin, for example, the light chain of Clostridial toxins, is reduced to half of the original concentration in a mammalian cell, such as in a mammalian neuron.

"Biological activity" or "activity" means the amount of cellular exocytosis inhibited from a cell per unit of time, such as exocytosis of a neurotransmitter from a neuron.

"Target cell" means a cell (including a neuron) with a binding affinity for a neurotoxin or for a modified neurotoxin.

SUMMARY

New structurally modified neurotoxins have been discovered. The present structurally modified neurotoxins can provide substantial benefits, for example, enhanced or decreased biological persistence and/or biological half-life and/or enhanced or decreased biological activity as compared to the unmodified neurotoxin.

In accordance with the present invention, there are provided structurally modified neurotoxins, which include a neurotoxin and a structural modification. The structural modification is effective to alter a biological persistence of the structurally modified neurotoxin relative to an identical neurotoxin without the structural modification. Also, the structurally modified neurotoxin is structurally different from a naturally existing neurotoxin.

The present invention also encompasses a modified neurotoxin comprising a neurotoxin with a structural modification, wherein said structural modification is effective to alter a biological activity of said modified neurotoxin relative to an identical neurotoxin without said structural modification, and wherein said modified neurotoxin is structurally different from a naturally existing neurotoxin. This structural modification can be effective to reduce an exocytosis from a target cell by more than the amount of the exocytosis reduced from the target cell by an identical neurotoxin without said structural modification. Alternately, the structural modification can be effective to reduce an exocytosis from a target cell by less than the amount of the exocytosis reduced from the cell by an identical neurotoxin without said structural modification. Significantly, the exocytosis can be exocytosis of a neurotransmitter and the modified neurotoxin can exhibit an altered biological activity without exhibiting an altered biological persistence. The structural modification can comprise a leucine-based motif. Additionally, the modified neurotoxin can exhibits an altered biological activity as well as an altered biological persistence. The present invention also includes the circumstances where: (a) the modified neurotoxin exhibits an increased biological activity as well as an increased biological persistence; (b) the modified neurotoxin exhibits an increased biological activity and a reduced biological persistence; (c) the modified neurotoxin exhibits a decreased biological activity and a decreased biological persistence, and; (d) the modified neurotoxin exhibits an decreased biological activity and an increased biological persistence.

Importantly, a unit amount (i.e. on a molar basis) of the modified neurotoxin can be more efficient to reduce an exocytosis from a cell than is a unit amount of the naturally existing neurotoxin. In other words, a unit amount of a modified neurotoxin, such as a modified botulinum toxin type A, can cleave its' intracellular substrate (SNAP) in a manner such that a greater inhibition of neurotransmitter exocytosis results (i.e. less neurotransmitter is released from the cell), as compared to the inhibition of neurotransmitter exocytosis exhibited by the naturally occurring neurotoxin.

Further in accordance with the present invention, are structurally modified neurotoxins, wherein a structural modification is effective to enhance a biological persistence of the modified neurotoxin. The enhanced biological persistence of the structurally modified neurotoxin can be due, at least in part, to an increased half-life and/or biological activity of the structurally modified neurotoxin.

Still further in accordance with the present invention, there are provided structurally modified neurotoxins wherein a biological persistence of the structurally modified neurotoxin is reduced relative to that of an identical neurotoxin without the structural modification. This reduction in biological persistence can be due, at least in part, to a decreased biological half-life and/or activity of the structurally modified neurotoxins.

Still further in accordance with the present invention, there are provided structurally modified neurotoxins wherein the structural modification comprises a number of amino acids. For example, the number of amino acids comprising the structural modification can be 1 or more amino acids, from 1 to about 22 amino acids, from 2 to about 10 amino acids, and from about 4 to about 7 amino acids.

In one embodiment, the structural modifications of the structurally modified neurotoxins can comprise an amino acid. The amino acid can comprise an R group containing a number of carbons. For example, the number of carbon atoms in the amino acid can be 1 or more, from 1 to about 20 carbons, from 1 to about 12 carbons, from 1 to about 9 carbons, from 2 to about 6 carbons, and about 4 carbons. R group as used in this application refers to amino acid side chains. For example, the R group for alanine is $CH_3$, and, for example, the R group for serine is $CH_2OH$.

In another embodiment, there are provided structurally modified neurotoxins wherein the modification comprises an amino acid. The amino acid can comprise an R group which is substantially hydrocarbyl.

In still another embodiment, there are provided structurally modified neurotoxins wherein the structural modification comprises an amino acid. The amino acid further can comprise an R group that includes at least one heteroatom.

Further in accordance with the present invention, there are provided structurally modified neurotoxins wherein the structural modification comprises, for example, a leucine-based motif, a tyrosine-based motif, and/or an amino acid derivative. Examples of an amino acid derivative that can comprise a structurally modified neurotoxin are a myristylated amino acid, an N-glycosylated amino acid, and a phosphorylated amino acid. The phosphorylated amino acids can be phosphorylated by, for example, casein kinase II, protein kinase C, and tyrosine kinase.

Still further in accordance with the present invention, there are provided structurally modified neurotoxins which can include a structural modification. The neurotoxin can comprise three amino acid sequence regions. The first region can be effective as a cellular binding moiety. This binding moiety can be a binding moiety for a target cell, such as a neuron. The binding moiety can be the carboxyl terminus of a botulinum toxin heavy chain. It is well known that the carboxyl terminus of a botulinum toxin heavy chain can be effective to bind, for example, receptors found on certain cells, including certain nerve cells. In one embodiment, the carboxyl terminus binds to receptors found on a presynaptic membrane of a nerve cell. The second region can be effective to translocate a structurally modified neurotoxin, or a part of a structurally modified neurotoxin across an endosome membrane. The third region can be effective to inhibit exocytosis from a target cell. The inhibition of exocytosis can be inhibition of neurotransmitter release, such as acetylcholine from a presynaptic membrane. For example, it is well known that the botulinum toxin light chain is effective to inhibit, for example, acetylcholine (as well as other neurotransmitters) release from various neuronal and non-neuronal cells.

At least one of the first, second or third regions can be substantially derived from a Clostridial neurotoxin. The third region can include the structural modification. In addition, the modified neurotoxin can be structurally different from a naturally existing neurotoxin. Also, the structural modification can be effective to alter a biological persistence of the modified neurotoxin relative to an identical neurotoxin without the structural modification.

In one embodiment, there are provided structurally modified neurotoxins, wherein the neurotoxin can be botulinum serotype A, B, $C_1$, $C_2$, D, E, F, G, tetanus toxin and/or mixtures thereof.

In another embodiment, there are provided structurally modified neurotoxins where the third region can be derived from botulinum toxin serotype A. In addition, there are provided structurally modified neurotoxins wherein the third region can not be derived from botulinum serotype A.

In still another embodiment, there are provided structurally modified neurotoxins wherein the structural modification includes a biological persistence enhancing component effective to enhance the biological persistence of the structurally modified neurotoxin. The enhancing of the biological persistence can be at least in part due to an increase in biological half-life and/or activity of the structurally modified neurotoxin.

Further in accordance with the present invention, there are provided structurally modified neurotoxins comprising a biological persistence enhancing component, wherein the biological persistence enhancing component can comprise a leucine-based motif. The leucine-based motif can comprise a run of 7 amino acids, where a quintet of amino acids and a duplet of amino acids can comprise the leucine-based motif. The quintet of amino acids can define the amino terminal end of the leucine-based motif. The duplet of amino acids can define the carboxyl end of the leucine-based motif. There are provided structurally modified neurotoxins wherein the quintet of amino acids can comprise one or more acidic amino acids. For example, the acidic amino acid can be glutamate or aspartate. The quintet of amino acids can comprise a hydroxyl containing amino acid. The hydroxyl containing amino acid can be, for example, a serine, a threonine or a tyrosine. This hydroxyl containing amino acid can be phosphorylated. At least one amino acid comprising the duplet of amino acids can be a leucine, isoleucine, methionine, alanine, phenylalanine, tryptophan, valine or tyrosine. In addition, the duplet of amino acids in the leucine-based motif can be leucine-leucine, leucine-isoleucine, isoleucine-leucine or isoleucine-isoleucine, leucine-methionine. The leucine-based motif can be an amino acid sequence of phenylalanine-glutamate-phenylalanine-tyrosine-lysine-leucine-leucine (SEQ ID NO: 1).

In one embodiment, there are provided structurally modified neurotoxins wherein the modification can be a tyrosine-based motif. The tyrosine-based motif can comprise four amino acids. The amino acid at the N-terminal end of the tyrosine-based motif can be a tyrosine. The amino acid at the C-terminal end of the tyrosine-based motif can be a hydrophobic amino acid.

Further in accordance with the present invention, the third region can be derived from botulinum toxin serotype A or form one of the other botulinum toxin serotypes.

Still further in accordance with the present invention, there are provided structurally modified neurotoxins where the biological persistence of the structurally modified neurotoxin can be reduced relative to an identical neurotoxin without the structural modification. The reduced biological persistence can be in part due a decreased biological half-life and/or to a decrease biological activity of the neurotoxin.

In one embodiment, there are provided structurally modified neurotoxins, where the structural modification can include a leucine-based motif with a mutation of one or more amino acids comprising the leucine-based motif. The mutation can be a deletion or substitution of one or more amino acids of the leucine-based motif.

In another embodiment, there are provided structurally modified neurotoxins, where the structural modification includes a tyrosine-based motif with a mutation of one or more amino acids comprising the tyrosine-based motif. For example, the mutation can be a deletion or substitution of one or more amino acids of the tyrosine-based motif.

In still another embodiment, there are provided structurally modified neurotoxins, wherein the structural modification comprises an amino acid derivative with a mutation of the amino acid derivative or a mutation to a nucleotide or amino acid sequence which codes for the derivativization of the amino acid. For example, a deletion or substitution of the derivatized amino acid or a nucleotide or amino acid sequence responsible for a derivatization of the derivatized amino acid. The amino acid derivative can be, for example, a myristylated amino acid, an N-glycosylated amino acid, or a phosphorylated amino acid. The phosphorylated amino acid can be produced by, for example, casein kinase II, protein kinase C or tyrosine kinase.

In one embodiment of the present invention, there are provided structurally modified neurotoxins, wherein the first, second and/or third regions of the structurally modified neurotoxins can be produced by recombinant DNA methodologies, i.e. produced recombinantly.

In another embodiment of the present invention, there are provided structurally modified neurotoxins, wherein the first, second and/or third region of the neurotoxin is isolated from a naturally existing Clostridial neurotoxin.

Another embodiment of the present invention provides a modified neurotoxin comprising a botulinum toxin (such as a botulinum toxin type A) which includes a structural modification which is effective to alter a biological persistence of the modified neurotoxin relative to an identical neurotoxin without the structural modification. The structural modification can comprise a deletion of amino acids 416 to 437 from the neurotoxin light chain of SEQ ID NO: 34 (FIG. 3).

In still another embodiment of the present invention there is provided a modified neurotoxin (such as a botulinum toxin type A) which includes a structural modification which is effective to alter a biological persistence of the modified neurotoxin relative to an identical neurotoxin without the structural modification. The structural modification can comprise a deletion of amino acids 1 to 8 from the neurotoxin light chain of SEQ ID NO: 34 (FIG. 3).

Still further in accordance with the present invention there is provided a modified neurotoxin, such as a botulinum toxin type A, which includes a structural modification which is effective to alter a biological persistence of the modified neurotoxin relative to an identical neurotoxin without the structural modification. The structural modification can comprise a deletion of amino acids 1 to 8 and 416 to 437 from the neurotoxin light chain of SEQ ID NO: 34 (FIG. 3).

Still further in accordance with the present invention, there is provided a modified botulinum toxin, such as a modified botulinum toxin type A, which includes a structural modification effective to alter a biological persistence of the modified neurotoxin relative to an identical neurotoxin without said structural modification. The structural modification can comprise a substitution of leucine at position 427 for an alanine and a substitution of leucine at position 428 for an alanine in a light chain of said neurotoxin (FIG. 3).

Additionally, the scope of the present invention also includes methods for enhancing the biological persistence and/or or for enhancing the biological activity of a neurotoxin. In these methods, a structural modification can be fused or added to the neurotoxin, for example, the structural modification can be a biological persistence enhancing component and/or a biological activity enhancing component. Examples of structural modifications that can be fused or added to the neurotoxin are a leucine-based motif, a tyrosine-based motif and an amino acid derivative. Examples of amino acid derivatives are a myristylated amino acid, an N-glycosylated amino acid, and a phosphorylated amino acid. An amino acid can be phosphorylated by, for example, protein kinase C, caseine kinase II or tyrosine kinase.

Also in accordance with the present invention, there are provided methods for reducing the biological persistence and/or for reducing the biological activity of a neurotoxin. These methods can comprise a step of mutating an amino acid of the neurotoxin. For example, an amino acid of a leucine-based motif within the neurotoxin can be mutated. Also, for example, one or more amino acids within a tyrosine-based motif of the neurotoxin can be mutated. Also, for example, an amino acid derivative for DNA or amino acid sequence responsible for the derivatization of the amino acid can be mutated. The derivatized amino acid can be a myristylated amino acid, a N-glycosylated amino acid, or a phosphorylated amino acid. The phosphorylated amino acid can be produced by, for example, protein kinase C, caseine kinase II and tyrosine kinase. These mutations can be, for example, amino acid deletions or amino acids substitutions.

The present invention also includes methods for treating a condition. The methods can comprise a step of administering an effective dose of a structurally modified neurotoxin to a mammal to treat a condition. The structurally modified neurotoxin can include a structural modification. The structural modification is effective to alter the biological persistence and/or the biological activity of the neurotoxin. These methods for treating a condition can utilize a neurotoxin that does not comprise a leucine-based motif. Also, these methods for treating a condition can utilize a neurotoxin, which includes a biological persistence enhancing component and/or a biological activity enhancing component. The biological persistence or activity enhancing component can comprise, for example, a tyrosine-based motif, a leucine-based motif or an amino acid derivative. The amino acid derivative can be, for example, a myristylated amino acid, an N-glycosylated amino acid or a phosphorylated amino acid. The phosphorylated amino acid can be produced by, for example, protein kinase C, caseine kinase II or tyrosine kinase. The condition treated can be a neuromuscular disorder, an autonomic disorder or pain. The treatment of a neuromuscular disorder can comprise a step of locally administering an effective amount of a modified neurotoxin to a muscle or a group of muscles. A method for treating an autonomic disorder can comprise a step of locally administering an effective amount of a modified neurotoxin to a gland or glands. A method for treating pain can comprise a step of administering an effective amount of a modified neurotoxin to the site of the pain. In addition, the treatment of pain can comprise a step of administering an effective amount of a modified neurotoxin to the spinal cord.

Still further in accordance with the present invention, there are provided methods for treating with modified neurotoxins conditions including spasmodic dysphonia, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity, spasmodic colitis, neurogenic bladder, anismus, limb spasticity, tics, tremors, bruxism, anal fissure, achalasia, dysphagia, lacrimation, hyperhydrosis, excessive salivation, excessive gastrointestinal secretions, pain from muscle spasms, headache pain, brow furrows and skin wrinkles.

BRIEF DESCRIPTION OF THE DRAWINGS

FIG. 3 shows the amino acid sequence for botulinum type A light chain. The amino acid sequence of SEQ ID NO: 34 shown, minus the underlined amino acids represents botulinum type A truncated light chain. The overline labeled ΔN8 indicates the eight amino acids deleted from the amino terminus of the light chain, the overline labeled ΔC22 indicates the 22 amino acids deleted from the carboxy terminus of the light chain. The double underline indicates the leucine-based motif and the dotted lines indicate tyrosine-based motifs.

FIG. 8 shows sequence alignment and consensus sequence for botulinum toxin type A HallA light chain of SEQ ID NO: 34 and botulinum toxin type B Danish I light chain of SEQ ID NO: 35.

DETAILED DESCRIPTION

Figure 1:
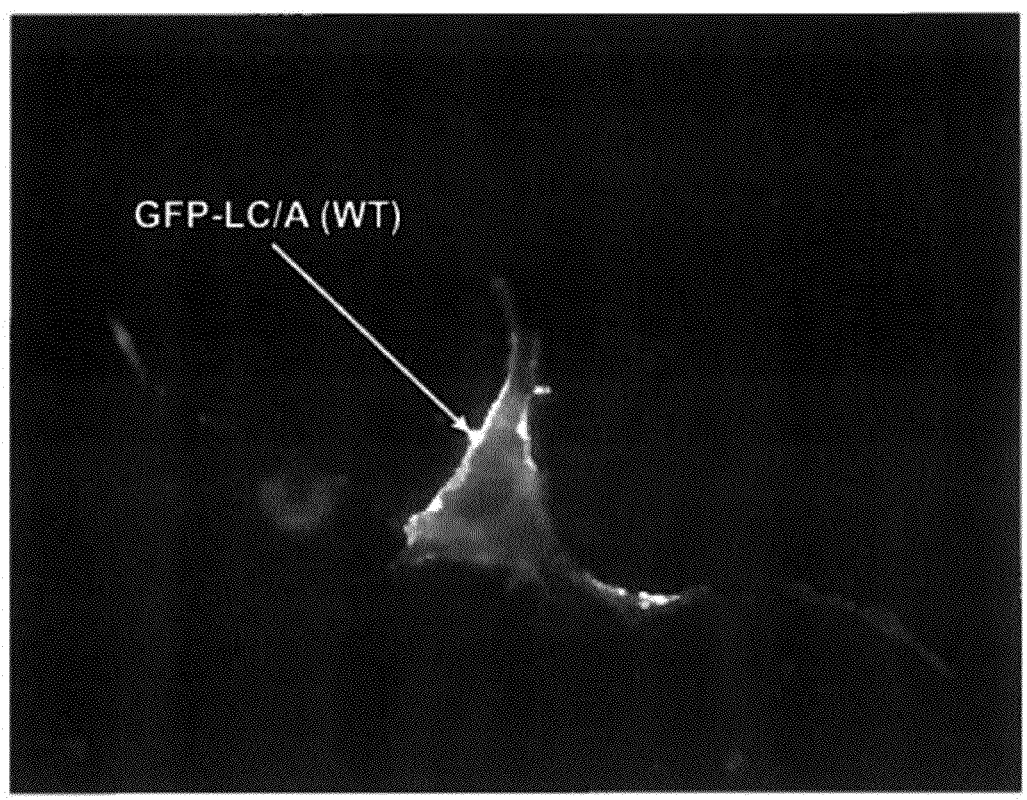
FIG. 1 shows localization of GFP-botulinum toxin A light chain in (nerve growth factor) NGF-differentiated live PC12 cells visualized on a fluorescence inverted microscope. The arrow indicates that GFP-botulinum toxin A light chain localizes to the plasma membrane.

The present invention is based upon the discovery that the biological persistence and/or the biological activity of a neurotoxin can be altered by structurally modifying the neurotoxin. In other words, a modified neurotoxin with an altered biological persistence and/or biological activity can be formed from a neurotoxin containing or including a structural modification. In one embodiment, the structural modification includes the fusing of a biological persistence enhancing component to the primary structure of a neurotoxin to enhance its biological persistence. In a preferred embodiment, the biological persistence enhancing component is a leucine-based motif. Even more preferably, the biological half-life and/or the biological activity of the modified neurotoxin is enhanced by about 100%. Generally speaking, the modified neurotoxin has a biological persistence of about 20% to 300% more than an identical neurotoxin without the structural modification. That is, for example, the modified neurotoxin including the biological persistence enhancing component is able to cause a substantial inhibition of neurotransmitter release for example, acetylcholine from a nerve terminal for about 20% to about 300% longer than a neurotoxin that is not modified.

The present invention also includes within its scope a modified neurotoxin with a biological activity altered as compared to the biological activity of the native or unmodified neurotoxin. For example, the modified neurotoxin can exhibit a reduced or an enhanced inhibition of exocytosis (such as exocytosis of a neurotransmitter) from a target cell with or without any alteration in the biological persistence of the modified neurotoxin.

In a broad embodiment of the present invention, a leucine-based motif is a run of seven amino acids. The run is organized into two groups. The first five amino acids starting from the amino terminal of the leucine-based motif form a "quintet of amino acids." The two amino acids immediately following the quintet of amino acids form a "duplet of amino acids." In a preferred embodiment, the duplet of amino acids is located at the carboxyl terminal region of the leucine-based motif. In another preferred embodiment, the quintet of amino acids includes at least one acidic amino acid selected from a group consisting of a glutamate and an aspartate.

The duplet of amino acid includes at least one hydrophobic amino acid, for example leucine, isoleucine, methionine, alanine, phenylalanine, tryptophan, valine or tyrosine. Preferably, the duplet of amino acid is a leucine-leucine, a leucine-isoleucine, an isoleucine-leucine or an isoleucine-isoleucine, leucine-methionine. Even more preferably, the duplet is a leucine-leucine.

In one embodiment, the leucine-based motif is XDXXXLL (SEQ ID NO: 14), wherein x can be any amino acids. In another embodiment, the leucine-based motif is XEXXXLL (SEQ ID NO: 15), wherein E is glutamic acid. In another embodiment, the duplet of amino acids can include an isoleucine or a methionine, forming XDXXXLI (SEQ ID NO: 16) or XDXXXLM (SEQ ID NO: 17), respectively. Additionally, the aspartic acid, D, can be replaced by a glutamic acid, E, to form XEXXXLI (SEQ ID NO: 18), XEXXXIL (SEQ ID NO: 19) and XEXXXLM (SEQ ID NO: 20). In a preferred embodiment, the leucine-based motif is SEQ ID NO: 1.

In another embodiment, the quintet of amino acids comprises at least one hydroxyl containing amino acid, for example, a serine, a threonine or a tyrosine. Preferably, the hydroxyl containing amino acid can be phosphorylated. More preferably, the hydroxyl containing amino acid is a serine which can be phosphorylated to allow for the binding of adapter proteins.

Although non-modified amino acids are provided as examples, a modified amino acid is also contemplated to be within the scope of this invention. For example, leucine-based motif can include a halogenated, preferably, fluorinated leucine.

Various leucine-based motif are found in various species. A list of possible leucine-based motif derived from the various species that can be used in accordance with this invention is shown in Table 1. This list is not intended to be limiting.

TABLE 1

| Species | Sequence | SEQ ID NO: |
| --- | --- | --- |
| Botulinum type A | FEFYKLL | 1 |
| Rat VMAT1 | EEKRAIL | 2 |
| Rat VMAT 2 | EEKMAIL | 3 |
| Rat VAChT | SERDVLL | 4 |
| Rat δ | VDTQVLL | 5 |
| Mouse δ | AEVQALL | 6 |
| Frog γ/δ | SDKQNLL | 7 |
| Chicken γ/δ | SDRQNLI | 8 |
| Sheep δ | ADTQVLM | 9 |
| Human CD3γ | SDKQTLL | 10 |
| Human CD4 | SQIKRLL | 11 |
| Human δ | ADTQALL | 12 |
| *S. cerevisiae* Vam3p | NEQSPLL | 13 |

VMAT is vesicular monoamine transporter; VAChT is vesicular acetylcholine transporter and *S. cerevisiae* Vam3p is a yeast homologue of synaptobrevin. Italicized serine residues are potential sites of phosphorylation.

The modified neurotoxin can be formed from any neurotoxin. Also, the modified neurotoxin can be formed from a fragment of a neurotoxin, for example, a botulinum toxin with a portion of the light chain and/or heavy chain removed. Preferably, the neurotoxin used is a Clostridial neurotoxin. A Clostridial neurotoxin comprises a polypeptide having three amino acid sequence regions. The first amino acid sequence region can include a target cell (i.e. a neuron) binding moiety which is substantially completely derived from a neurotoxin selected from a group consisting of beratti toxin; butyricum toxin; tetanus toxin; botulinum type A, B, C$_1$, D, E, F, and G. Preferably, the first amino acid sequence region is derived from the carboxyl terminal region of a toxin heavy chain, H$_C$. Also, the first amino acid sequence region can comprise a targeting moiety which can comprise a molecule (such as an amino acid sequence) that can bind to a receptor, such as a cell surface protein or other biological component on a target cell.

The second amino acid sequence region is effective to translocate the polypeptide or a part thereof across an endosome membrane into the cytoplasm of a neuron. In one embodiment, the second amino acid sequence region of the polypeptide comprises an amine terminal of a heavy chain, $H_N$, derived from a neurotoxin selected from a group consisting of beratti toxin; butyricum toxin; tetanus toxin; botulinum type A, B, $C_1$, D, E, F, and G.

The third amino acid sequence region has therapeutic activity when it is released into the cytoplasm of a target cell, such as a neuron. In one embodiment, the third amino acid sequence region of the polypeptide comprises a toxin light chain, L, derived from a neurotoxin selected from a group consisting of beratti toxin; butyricum toxin; tetanus toxin; botulinum type A, B, $C_1$, D, E, F, and G.

The Clostridial neurotoxin can be a hybrid neurotoxin. For example, each of the neurotoxin's amino acid sequence regions can be derived from a different Clostridial neurotoxin serotype. For example, in one embodiment, the polypeptide comprises a first amino acid sequence region derived from the $H_C$ of the tetanus toxin, a second amino acid sequence region derived from the $H_N$ of botulinum type B, and a third amino acid sequence region derived from the light chain of botulinum serotype E. All other possible combinations are included within the scope of the present invention.

Alternatively, all three of the amino acid sequence regions of the Clostridial neurotoxin can be from the same species and same serotype. If all three amino acid sequence regions of the neurotoxin are from the same Clostridial neurotoxin species and serotype, the neurotoxin will be referred to by the species and serotype name. For example, a neurotoxin polypeptide can have its first, second and third amino acid sequence regions derived from Botulinum type E. In which case, the neurotoxin is referred as Botulinum type E.

Additionally, each of the three amino acid sequence regions can be modified from the naturally occurring sequence from which they are derived. For example, the amino acid sequence region can have at least one or more amino acids added or deleted as compared to the naturally occurring sequence.

A biological persistence enhancing component or a biological activity enhancing component, for example a leucine-based motif, can be fused with any of the above described neurotoxins to form a modified neurotoxin with an enhanced biological persistence and/or an enhanced biological activity. "Fusing" as used in the context of this invention includes covalently adding to or covalently inserting in between a primary structure of a neurotoxin. For example, a biological persistence enhancing component and/or a biological activity enhancing component can be added to a Clostridial neurotoxin which does not have a leucine-based motif in its primary structure. In one embodiment, a leucine-based motif is fused with a hybrid neurotoxin, wherein the third amino acid sequence is derived from botulinum serotype A, B, $C_1$, $C_2$, D, E, F, or G. In another embodiment, the leucine-based motif is fused with a botulinum type E.

In another embodiment, a biological persistence enhancing component and/or a biological activity enhancing component is added to a neurotoxin by altering a cloned DNA sequence encoding the neurotoxin. For example, a DNA sequence encoding a biological persistence enhancing component and/or a biological activity enhancing component is added to a cloned DNA sequence encoding the neurotoxin into which the biological persistence enhancing component and/or a biological activity enhancing component is to be added. This can be done in a number of ways which are familiar to a molecular biologist of ordinary skill. For example, site directed mutagenesis or PCR cloning can be used to produce the desired change to the neurotoxin encoding DNA sequence.

The DNA sequence can then be reintroduced into a native host strain. In the case of botulinum toxins the native host strain would be a *Clostridium botulinum* strain. Preferably, this host strain will be lacking the native botulinum toxin gene. In an alternative method, the altered DNA can be introduced into a heterologous host system such as *E. coli* or other prokaryotes, yeast, insect cell lines or mammalian cell lines. Once the altered DNA has been introduced into its host, the recombinant toxin containing the added biological persistence enhancing component and/or a biological activity enhancing component can be produced by, for example, standard fermentation methodologies.

Similarly, a biological persistence enhancing component can be removed from a neurotoxin. For example, site directed mutagenesis can be used to eliminate biological persistence enhancing components, for example, a leucine-based motif.

Standard molecular biology techniques that can be used to accomplish these and other genetic manipulations are found in Sambrook et al. (1989) which is incorporated in its entirety herein by reference.

In one embodiment, the leucine-based motif is fused with, or added to, the third amino acid sequence region of the neurotoxin. In a preferred embodiment, the leucine-based motif is fused with, or added to, the region towards the carboxylic terminal of the third amino acid sequence region. More preferably, the leucine-based motif is fused with, or added to, the carboxylic terminal of the third region of a neurotoxin. Even more preferably, the leucine-based motif is fused with, or added to the carboxylic terminal of the third region of botulinum type E. The third amino acid sequence to which the leucine-based motif is fused or added can be a component of a hybrid or chimeric modified neurotoxin. For example, the leucine-based motif can be fused to or added to the third amino acid sequence region (or a part thereof) of one botulinum toxin type (i.e. a botulinum toxin type A), where the leucine-based motif-third amino acid sequence region has itself been fused to or conjugated to first and second amino acid sequence regions from another type (or types) of a botulinum toxin (such as botulinum toxin type B and/or E).

In another embodiment, a structural modification of a neurotoxin which has a pre-existing biological persistence enhancing component and/or a biological activity enhancing component, for example, a leucine-based motif includes deleting or substituting one or more amino acids of the leucine-based motif. In addition, a modified neurotoxin includes a structural modification which results in a neurotoxin with one or more amino acids deleted or substituted in the leucine-based motif. The removal or substitution of one or more amino acids from the preexisting leucine-based motif is effective to reduce the biological persistence and/or a biological activity of a modified neurotoxin. For example, the deletion or substitution of one or more amino acids of the leucine-based motif of botulinum type A reduces the biological half-life and/or the biological activity of the modified neurotoxin.

Amino acids that can be substituted for amino acids contained in a biological persistence enhancing component include alanine, asparagine, cysteine, aspartic acid, glutamic acid, phenylalanine, glycine, histidine, isoleucine, lysine, leucine, methionine, proline, glutamine, arginine, serine, threonine, valine, tryptophan, tyrosine and other naturally occurring amino acids as well as non-standard amino acids.

In the present invention the native botulinum type A light chain has been shown to localize to differentiated PC12 cell membranes in a characteristic pattern. Biological persistence enhancing components are shown to substantially contribute to this localization.

The data of the present invention demonstrates that when the botulinum toxin type A light chain is truncated or when the leucine-based motif is mutated, the light chain substantially loses its ability to localize to the membrane in its characteristic pattern. Localization to the cellular membrane is believed to be a key factor in determining the biological persistence and/or the biological activity of a botulinum toxin. This is because localization to a cell membrane can protect the localized protein from inter-cellular protein degrading.

Figure 2:
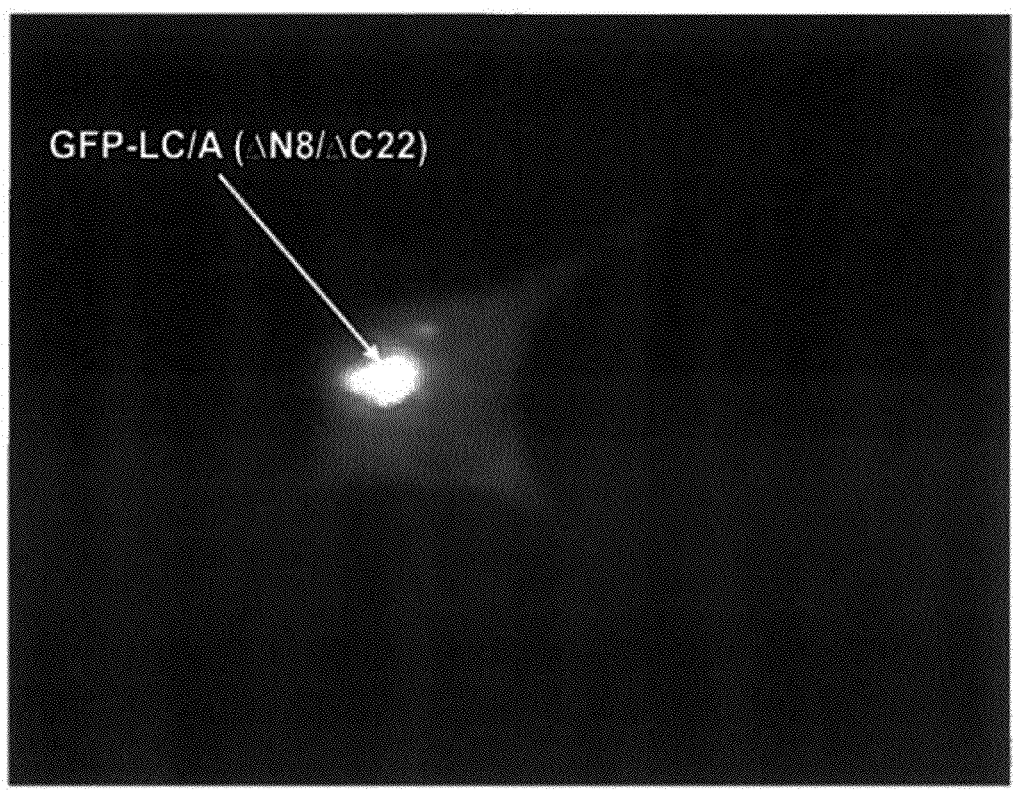
FIG. 2 shows the localization of GFP-truncated botulinum toxin A light chain in NGF-differentiated live PC12 cells visualized on a fluorescence inverted microscope. The arrow indicates that GFP-truncated botulinum toxin A light chain localizes to punctate bodies inside the cytoplasm.

FIGS. 1 and 2 show that deletion of the leucine-based motif from the light chain of botulinum type A can change membrane localization of the type A light chain. FIG. 1 shows localization of GFP-light chain A fusion protein in differentiated PC12 cells. The GFP fusion proteins were produced and visualized in differentiated PC12 cells using methods well known to those skilled in the art, for example, as described in Galli et al (1998) Mol Biol Cell 9:1437-1448, incorporated in its entirety herein by reference; also, for example, as described in Martinez-Arca et al (2000) J Cell Biol 149:889-899, also incorporated in its entirety herein by reference. Localization of a GFP-truncated light chain A is shown in FIG. 2. Comparing FIGS. 1 and 2, it can be seen that the pattern of localization is completely altered by the deletion of the N-terminus and C-terminus comprising the leucine-based motif. FIG. 3 shows the amino acid sequence of the botulinum type A light chain of SEQ ID NO: 34. The underlined amino acid sequences indicate the amino acids that were deleted in the truncated mutant. The leucine-based motif is indicated by the asterisked bracket.

Figure 4:
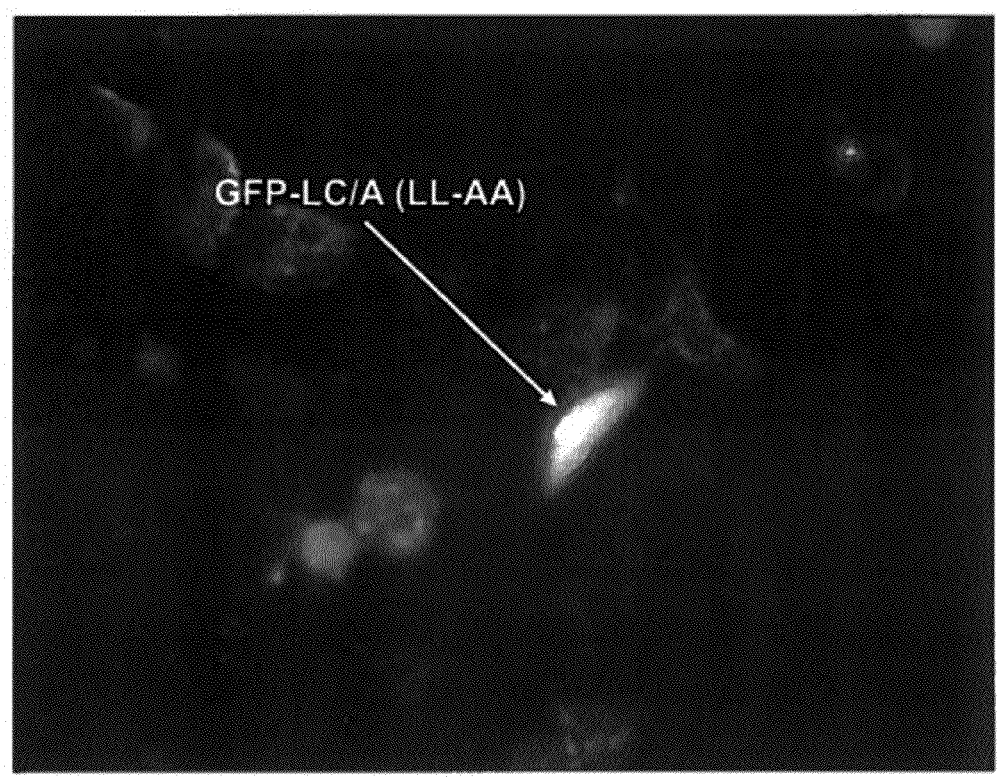
FIG. 4 shows the localization of GFP-botulinum toxin A light chain with LL to AA mutation at position 427 and 428 in NGF-differentiated live PC12 cells visualized on a fluorescence inverted microscope. The arrow indicates that GFP-botulinum toxin A light chain with LL to AA mutation localizes to punctate bodies inside the cytoplasm.

Further studies have been done in the present invention to analyze the effect of specific amino acid substitutions within the leucine-based motif. For example, in one study both leucine residues contained in the leucine-based motif were substituted for alanine residues. FIG. 4 shows the fluorescent image of differentiated PC12 cells transfected with DNA encoding this di-leucine to di-alanine substituted GFP-botulinum A light chain. As can be seen, the substitution of alanine for leucine at positions 427 and 428 in the botulinum type A light chain substantially changes the localization characteristic of the light chain.

Figure 6:
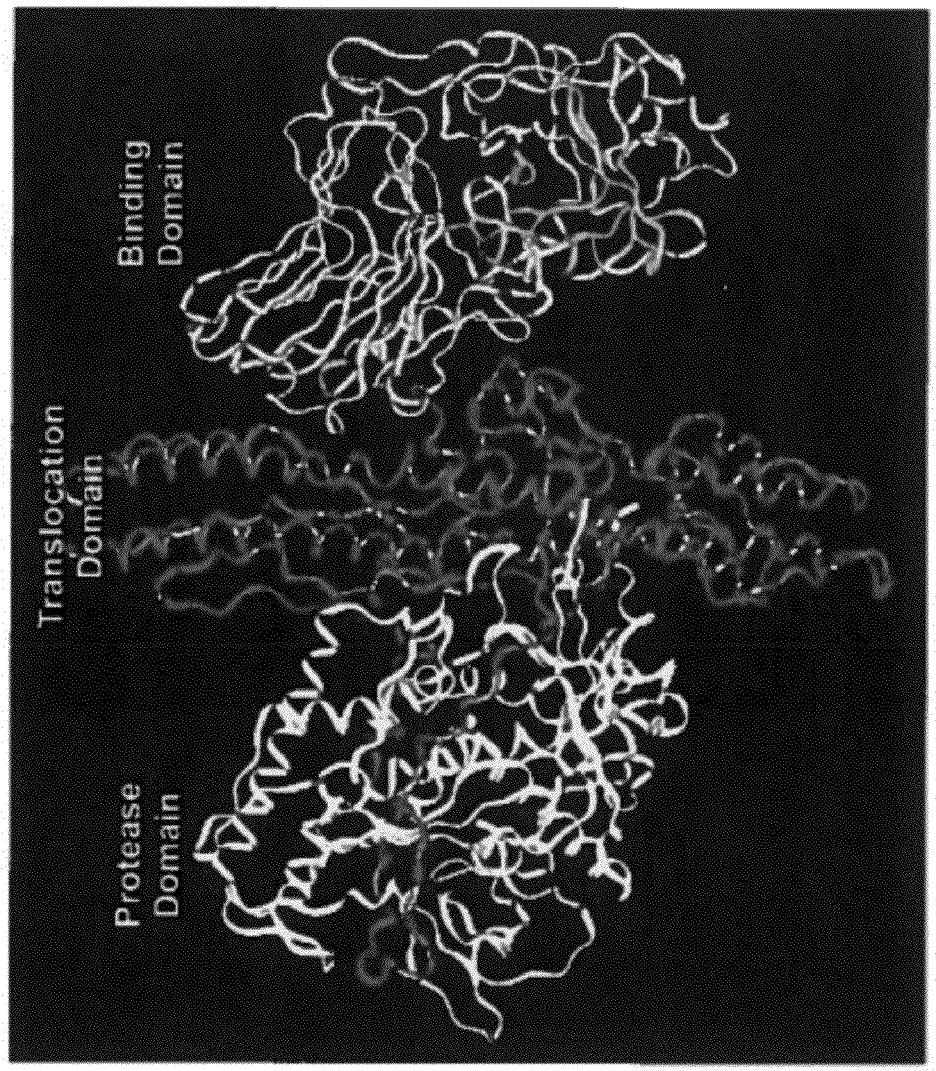
FIG. 6 shows an X-ray crystalographic structure of botulinum toxin type A.

It is within the scope of this invention that a leucine-based motif, or any other persistence enhancing component and/or a biological activity enhancing component present on a light chain, can be used to protect the heavy chain as well. A random coil belt extends from the botulinum type A translocation domain and encircles the light chain. It is possible that this belt keeps the two subunits in proximity to each other inside the cell while the light chain is localized to the cell membrane. The structure of native botulinum toxin type A is shown in FIG. 6.

Figure 5:
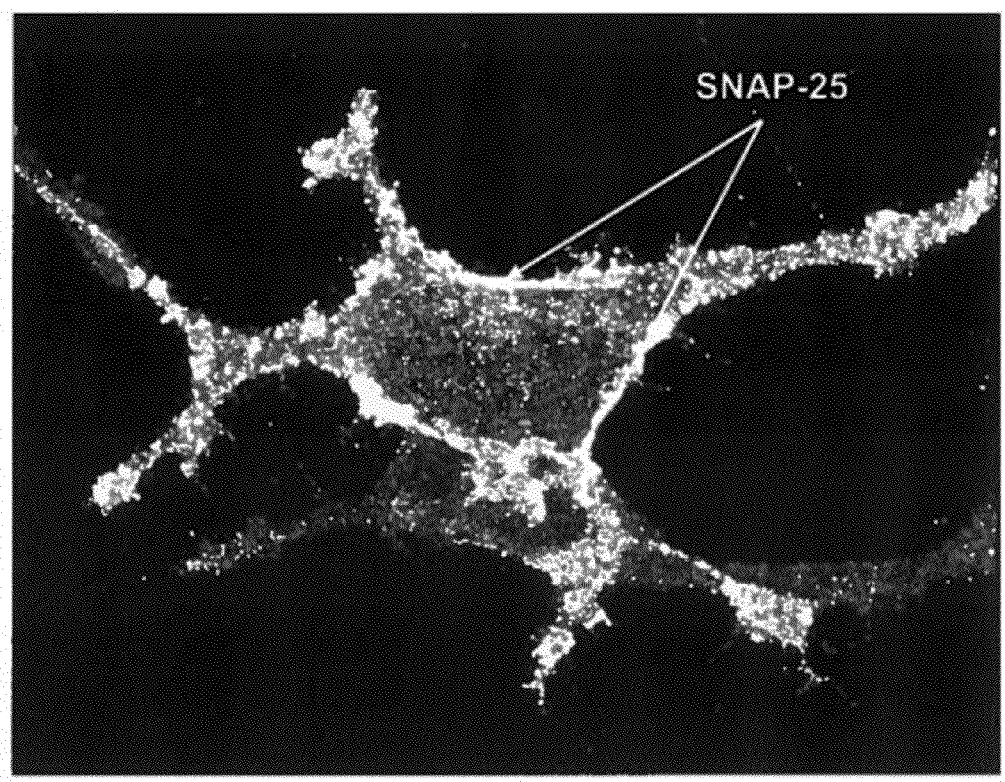
FIG. 5 shows localization of fluorescently labeled anti-SNAP-25 visualized in horizontal confocal sections of staurosporine-differentiated PC12 cells. The arrow indicates that SNAP-25 localizes to the plasma membrane.

In addition, the data of the present invention shows that the leucine-based motif can be valuable in localizing the botulinum A toxin in close proximity to the SNAP-25 substrate within the cell. This can mean that the leucine-based motif is important not only for determining the half-life of the toxin but for determining the activity of the toxin as well. That is, the toxin will have a greater activity if it is maintained in close proximity to the SNAP-25 substrate inside the cell. FIG. 5 shows the localization of SNAP-25 in horizontal confocal sections of differentiated PC12 cells (from Martinez-Arca et al (2000) J Cell Biol 149:889-899). Similarity in the pattern of localization can be seen when comparing localization of botulinum type A light chain as seen in FIG. 1 to localization of SNAP-25 seen in FIG. 5.

The data of the present invention clearly shows that truncation of the light chain, thereby deleting the leucine-based motif, or amino acid substitution within the leucine-based motif substantially changes membrane localization of the botulinum type A light chain in nerve cells. In both truncation and substitution a percentage of the altered light chain can localize to the cell membrane in a pattern unlike that of the native type A light chain (see FIGS. 1, 2 and 4). This data supports the presence of biological persistence enhancing components other than a leucine-based motif such as tyrosine motifs and amino acid derivatives. Use of these other biological persistence enhancing components and/or a biological activity enhancing components in modified neurotoxins is also within the scope of the present invention.

Also within the scope of the present invention is more than one biological persistence enhancing component used in combination in a modified neurotoxin to alter biological persistence of the neurotoxin that is modified. The present invention also includes use of more than one biological activity enhancing or biological activity reducing components used in combination in a modified neurotoxin to alter the biological activity of the neurotoxin that is modified.

Tyrosine-based motifs are within the scope of the present invention as biological persistence and/or a biological activity altering components. Tyrosine-based motifs comprise the sequence Y-X-X-Hy (SEQ ID NO: 21), where Y is tyrosine, X is any amino acid and Hy is a hydrophobic amino acid. Tyrosine-based motifs can act in a manner that is similar to that of leucine-based motifs. In FIG. 3 some of tyrosine motifs found in the type A toxin light chain are bracketed. In addition, a tyrosine-based motif is found within the leucine-based motif which is indicated by an asterisked bracket in FIG. 3.

Also within the scope of the present invention are modified neurotoxins which comprise one or more biological persistence altering components and/or a biological activity enhancing components which occur naturally in both botulinum toxin types A and B.

Figure 7:
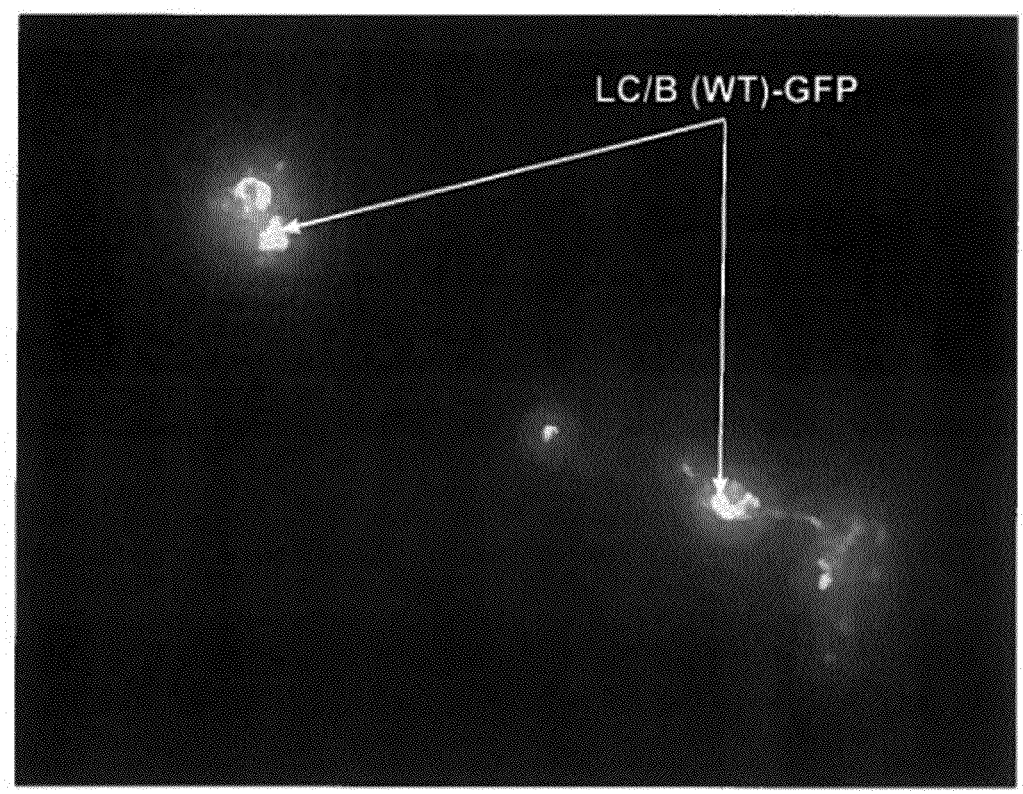
FIG. 7 shows localization of GFP-botulinum type B neurotoxin light chain in NGF-differentiated live PC12 cells visualized on a fluorescence inverted microscope. The arrow indicates that GFP-botulinum toxin B light chain localizes to punctate bodies inside the cytoplasm.

FIG. 7 shows localization of GFP-botulinum type B neurotoxin light chain in live, differentiated PC12 cells. Localization of the type B light chain appears to be to an intracellular organelle. Similar localization pattern is seen for GFP-truncated botulinum type A shown in FIG. 2. Localization of a botulinum toxin, or botulinum toxin light chain, within the cell is believed to be a key factor in determining biological persistence and/or biological activity of the toxin. Therefore, these data appear to indicate that there are biological persistence altering component(s), and/or biological activity altering component(s), common to the type A and type B botulinum toxins. These, and other biological persistence altering components, and biological activity altering components, are contemplated for use in accordance with the present invention.

FIG. 8 shows a sequence alignment between type A and type B light chains isolated from strains type A HallA (SEQ ID NO: 34) and type B Danish I (SEQ ID NO: 35) respectively. Light chains or heavy chains isolated from other strains of botulinum toxin types A and B can also be used for sequence comparison. The shaded amino acids represent amino acid identities, or matches, between the chains. Each of the blocked amino acids between amino acid position 10 and amino acid position 425 of SEQ ID NO: 34 (FIG. 8), alone or in combination with any other shaded amino acid or amino acids, represents a biological persistence altering component that is within the scope of the present invention. For example, amino acids KAFK (SEQ ID NO: 53) at positions 35 to 38 of SEQ ID NO: 39, LNK at positions 304 to 306 of SEQ ID NO: 39, L at position 228 of SEQ ID NO: 39 in combination with KL at positions 94 and 95 of SEQ ID NO: 39, FDKLYK (SEQ ID NO: 23) at positions 346 to 351 of SEQ ID NO: 39, YLXT (SEQ ID NO: 52) at positions 78 to 81 of SEQ ID NO: 39, YYD at positions 73 to 75 of SEQ ID NO: 39 in combination with YL at positions 78 and 79 of SEQ ID NO: 39 in combination with T a position 81 of SEQ ID NO: 39, F at position 297 of SEQ ID NO: 39 in combination with I at position 300 of SEQ ID NO: 39 in combination with KL at positions 94 and 95 of SEQ ID NO: 39 can be biological persistence altering components for use within the scope of this invention. Additional biological altering components include SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, and SEQ ID NO: 51. In addition, conserved regions of charge, hydrophobicity, hydrophilicity and/or conserved secondary, tertiary, or quaternary structures that may be independent of conserved sequence are within the scope of the present invention.

Amino acid derivatives are also within the scope of the present invention as biological persistence enhancing components and/or as biological activity enhancing components. Examples of amino acid derivatives that act to effect biological persistence and/or biological activity are phosphorylated amino acids. These amino acids include, for example, amino acids phosphorylated by tyrosine kinase, protein kinase C or casein kinase II. Other amino acid derivatives within the scope of the present invention as biological persistence enhancing components and/or as biological activity enhancing components are myristylated amino acids and N-glycosylated amino acids.

In one broad aspect of the present invention, a method is provided for treating a condition using a modified neurotoxin. The conditions can include, for example, skeletal muscle conditions, smooth muscle conditions, pain and glandular conditions. The modified neurotoxin can also be used for cosmetics, for example, to treat brow furrows.

The neuromuscular disorders and conditions that can be treated with a modified neurotoxin include: for example, spasmodic dysphonia, laryngeal dystonia, oromandibular and lingual dystonia, cervical dystonia, focal hand dystonia, blepharospasm, strabismus, hemifacial spasm, eyelid disorders, spasmodic torticolis, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups can be treated using the present methods of administration. Other examples of conditions that can be treated using the present methods and compositions are lacrimation, hyperhydrosis, excessive salivation and excessive gastrointestinal secretions, as well as other secretory disorders. In addition, the present invention can be used to treat dermatological conditions, for example, reduction of brow furrows, reduction of skin wrinkles. The present invention can also be used in the treatment of sports injuries.

Borodic U.S. Pat. No. 5,053,005 discloses methods for treating juvenile spinal curvature, i.e. scoliosis, using botulinum type A. The disclosure of Borodic is incorporated in its entirety herein by reference. In one embodiment, using substantially similar methods as disclosed by Borodic, a modified neurotoxin can be administered to a mammal, preferably a human, to treat spinal curvature. In a preferred embodiment, a modified neurotoxin comprising botulinum type E fused with a leucine-based motif is administered. Even more preferably, a modified neurotoxin comprising botulinum type A-E with a leucine-based motif fused to the carboxyl terminal of its light chain is administered to the mammal, preferably a human, to treat spinal curvature.

In addition, the modified neurotoxin can be administered to treat other neuromuscular disorders using well known techniques that are commonly performed with botulinum type A. For example, the present invention can be used to treat pain, for example, headache pain, pain from muscle spasms and various forms of inflammatory pain. For example, Aoki U.S. Pat. No. 5,721,215 and Aoki U.S. Pat. No. 6,113,915 disclose methods of using botulinum toxin type A for treating pain. The disclosure of these two patents is incorporated in its entirety herein by reference.

Autonomic nervous system disorders can also be treated with a modified neurotoxin. For example, glandular malfunctioning is an autonomic nervous system disorder. Glandular malfunctioning includes excessive sweating and excessive salivation. Respiratory malfunctioning is another example of an autonomic nervous system disorder. Respiratory malfunctioning includes chronic obstructive pulmonary disease and asthma. Sanders et al. disclose methods for treating the autonomic nervous system; for example, treating autonomic nervous system disorders such as excessive sweating, excessive salivation, asthma, etc., using naturally existing botulinum toxins. The disclosure of Sander et al. is incorporated in its entirety by reference herein. In one embodiment, substantially similar methods to that of Sanders et al. can be employed, but using a modified neurotoxin, to treat autonomic nervous system disorders such as the ones discussed above. For example, a modified neurotoxin can be locally applied to the nasal cavity of the mammal in an amount sufficient to degenerate cholinergic neurons of the autonomic nervous system that control the mucous secretion in the nasal cavity.

Pain that can be treated by a modified neurotoxin includes pain caused by muscle tension, or spasm, or pain that is not associated with muscle spasm. For example, Binder in U.S. Pat. No. 5,714,468 discloses that headache caused by vascular disturbances, muscular tension, neuralgia and neuropathy can be treated with a naturally occurring botulinum toxin, for example Botulinum type A. The disclosures of Binder are incorporated in its entirety herein by reference. In one embodiment, substantially similar methods to that of Binder can be employed, but using a modified neurotoxin, to treat headache, especially the ones caused by vascular disturbances, muscular tension, neuralgia and neuropathy. Pain caused by muscle spasm can also be treated by an administration of a modified neurotoxin. For example, a botulinum type E fused with a leucine-based motif, preferably at the carboxyl terminal of the botulinum type E light chain, can be administered intramuscularly at the pain/spasm location to alleviate pain.

Furthermore, a modified neurotoxin can be administered to a mammal to treat pain that is not associated with a muscular disorder, such as spasm. In one broad embodiment, methods of the present invention to treat non-spasm related pain include central administration or peripheral administration of the modified neurotoxin.

For example, Foster et al. in U.S. Pat. No. 5,989,545 discloses that a botulinum toxin conjugated with a targeting moiety can be administered centrally (intrathecally) to alleviate pain. The disclosures of Foster et al. are incorporated in its entirety by reference herein. In one embodiment, substantially similar methods to that of Foster et al. can be employed, but using the modified neurotoxin according to this invention, to treat pain. The pain to be treated can be an acute pain, or preferably, chronic pain.

An acute or chronic pain that is not associated with a muscle spasm can also be alleviated with a local, peripheral administration of the modified neurotoxin to an actual or a perceived pain location on the mammal. In one embodiment, the modified neurotoxin is administered subcutaneously at or near the location of pain, for example, at or near a cut. In another embodiment, the modified neurotoxin is administered intramuscularly at or near the location of pain, for example, at or near a bruise location on the mammal. In another embodiment, the modified neurotoxin is injected directly into a joint of a mammal, for treating or alleviating pain caused by arthritic conditions. Also, frequent repeated injection or infusion of the modified neurotoxin to a peripheral pain location is within the scope of the present invention. However, given the long lasting therapeutic effects of the present invention, frequent injection or infusion of the neurotoxin can not be necessary. For example, practice of the present invention can provide an analgesic effect, per injection, for 2 months or longer, for example 27 months, in humans.

Without wishing to limit the invention to any mechanism or theory of operation, it is believed that when the modified neurotoxin is administered locally to a peripheral location, it inhibits the release of Neuro-substances, for example substance P, from the peripheral primary sensory terminal by inhibiting SNARE-dependent exocytosis. Since the release of substance P by the peripheral primary sensory terminal can cause or at least amplify pain transmission process, inhibition of its release at the peripheral primary sensory terminal will dampen the transmission of pain signals from reaching the brain.

In addition to having pharmacologic actions at the peripheral location, the modified neurotoxin of the present invention can also have inhibitory effects in the central nervous system, upon direct intrathecal administration, as set forth in U.S. Pat. No. 6,113,915, or upon peripheral administration, where presumably the modified toxin acts through retrograde transport via a primary sensory afferent. This hypothesis of retrograde axonal transport is supported by published data which shows that botulinum type A can be retrograde transported to the dorsal horn when the neurotoxin is injected peripherally. Thus, work by Weigand et al, *Nauny-Schmiedeberg's Arch. Pharmacol.* 1976; 292, 161-165, and Habermann, *Nauny-Schmiedeberg's Arch. Pharmacol.* 1974; 281, 47-56, showed that botulinum toxin is able to ascend to the spinal area by retrograde transport. As such, a modified neurotoxin, for example botulinum type A with one or more amino acids mutated from the leucine-based motif, injected at a peripheral location, for example intramuscularly, can be expected to be retrograde transported from the peripheral primary sensory terminal to a central region.

The amount of the modified neurotoxin administered can vary widely according to the particular disorder being treated, its severity and other various patient variables including size, weight, age, and responsiveness to therapy. Generally, the dose of modified neurotoxin to be administered will vary with the age, presenting condition and weight of the mammal, preferably a human, to be treated. The potency of the modified neurotoxin will also be considered.

Assuming a potency (for a botulinum toxin type A) which is substantially equivalent to $LD_{50}$=2,730 U in a human patient and an average person is 75 kg, a lethal dose (for a botulinum toxin type A) would be about 36 U/kg of a modified neurotoxin. Therefore, when a modified neurotoxin with such an $LD_{50}$ is administered, it would be appropriate to administer less than 36 U/kg of the modified neurotoxin into human subjects. Preferably, about 0.01 U/kg to 30 U/kg of the modified neurotoxin is administered. More preferably, about 1 U/kg to about 15 U/kg of the modified neurotoxin is administered. Even more preferably, about 5 U/kg to about 10 U/kg modified neurotoxin is administered. Generally, the modified neurotoxin will be administered as a composition at a dosage that is proportionally equivalent to about 2.5 cc/100 U. Those of ordinary skill in the art will know, or can readily ascertain, how to adjust these dosages for neurotoxin of greater or lesser potency. It is known that botulinum toxin type B can be administered at a level about fifty times higher that that used for a botulinum toxin type A for similar therapeutic effect. Thus, the units amounts set forth above can be multiplied by a factor of about fifty for a botulinum toxin type B.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill). For example, the route and dosage for administration of a modified neurotoxin according to the present disclosed invention can be selected based upon criteria such as the solubility characteristics of the modified neurotoxin chosen as well as the types of disorder being treated.

The modified neurotoxin can be produced by chemically linking the leucine-based motif to a neurotoxin using conventional chemical methods well known in the art. For example, botulinum type E can be obtained by establishing and growing cultures of *Clostridium botulinum* in a fermenter, and then harvesting and purifying the fermented mixture in accordance with known procedures.

The modified neurotoxin can also be produced by recombinant techniques. Recombinant techniques are preferable for producing a neurotoxin having amino acid sequence regions from different Clostridial species or having modified amino acid sequence regions. Also, the recombinant technique is preferable in producing botulinum type A with the leucine-based motif being modified by deletion. The technique includes steps of obtaining genetic materials from natural sources, or synthetic sources, which have codes for a cellular binding moiety, an amino acid sequence effective to translocate the neurotoxin or a part thereof, and an amino acid sequence having therapeutic activity when released into a cytoplasm of a target cell, preferably a neuron. In a preferred embodiment, the genetic materials have codes for the biological persistence enhancing component, preferably the leucine-based motif, the $H_C$, the $H_N$ and the light chain of the Clostridial neurotoxins and fragments thereof. The genetic constructs are incorporated into host cells for amplification by first fusing the genetic constructs with a cloning vectors, such as phages or plasmids. Then the cloning vectors are inserted into a host, for example, *Clostridium* sp., *E. coli* or other prokaryotes, yeast, insect cell line or mammalian cell lines. Following the expressions of the recombinant genes in host cells, the resultant proteins can be isolated using conventional techniques.

There are many advantages to producing these modified neurotoxins recombinantly. For example, to form a modified neurotoxin, a modifying fragment, or component must be attached or inserted into a neurotoxin. The production of neurotoxin from anaerobic *Clostridium* cultures is a cumbersome and time-consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL-3). During the fermentation process, the folded single-chain neurotoxins are activated by endogenous Clostridial proteases through a process termed nicking to create a dichain. Sometimes, the process of nicking involves the removal of approximately 10 amino acid residues from the single-chain to create the dichain form in which the two chains remain covalently linked through the intrachain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the serotype and amounts of proteolytic activity produced by a given strain. For example, greater than 99% of *Clostridial botulinum* serotype A single-chain neurotoxin is activated by the Hall A *Clostridial botulinum* strain, whereas serotype B and E strains produce toxins with lower amounts of activation (0 to 75% depending upon the fermentation time). Thus, the high toxicity of the mature neurotoxin plays a major part in the commercial manufacture of neurotoxins as therapeutic agents.

The degree of activation of engineered *Clostridial* toxins is, therefore, an important consideration for manufacture of these materials. It would be a major advantage if neurotoxins such as botulinum toxin and tetanus toxin could be expressed, recombinantly, in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in *E. coli* and purification of individual H and light chains of tetanus and botulinum toxins; these isolated chains are, by themselves, non-toxic; see Li et al., *Biochemistry* 33:7014-7020 (1994); Zhou et al., *Biochemistry* 34:15175-15181 (1995), hereby incorporated by reference herein. Following the separate production of these peptide chains and under strictly controlled conditions the H and light chains can be combined by oxidative disulphide linkage to form the neuroparalytic di-chains.

EXAMPLES

The following non-limiting examples provide those of ordinary skill in the art with specific preferred methods to treat non-spasm related pain within the scope of the present invention and are not intended to limit the scope of the invention.

Example 1

Treatment of Pain Associated with Muscle Disorder

An unfortunate 36 year old woman has a 15 year history of temporomandibular joint disease and chronic pain along the masseter and temporalis muscles. Fifteen years prior to evaluation she noted increased immobility of the jaw associated with pain and jaw opening and closing and tenderness along each side of her face. The left side is originally thought to be worse than the right. She is diagnosed as having temporomandibular joint (TMJ) dysfunction with subluxation of the joint and is treated with surgical orthoplasty meniscusectomy and condyle resection.

She continues to have difficulty with opening and closing her jaw after the surgical procedures and for this reason, several years later, a surgical procedure to replace prosthetic joints on both sides is performed. After the surgical procedure progressive spasms and deviation of the jaw ensues. Further surgical revision is performed subsequent to the original operation to correct prosthetic joint loosening. The jaw continues to exhibit considerable pain and immobility after these surgical procedures. The TMJ remained tender as well as the muscle itself. There are tender points over the temporomandibular joint as well as increased tone in the entire muscle. She is diagnosed as having post-surgical myofascial pain syndrome and is injected with the modified neurotoxin into the masseter and temporalis muscles; the modified neurotoxin is botulinum type E comprising a leucine-based motif. The particular dose as well as the frequency of administrations depends upon a variety of factors within the skill of the treating physician.

Several days after the injections she noted substantial improvement in her pain and reports that her jaw feels looser. This gradually improves over a 2 to 3 week period in which she notes increased ability to open the jaw and diminishing pain. The patient states that the pain is better than at any time in the last 4 years. The improved condition persists for up to 27 months after the original injection of the modified neurotoxin.

Example 2

Treatment of Pain Subsequent to Spinal Cord Injury

A patient, age 39, experiencing pain subsequent to spinal cord injury is treated by intrathecal administration, for example, by spinal tap or by catherization (for infusion) to the spinal cord, with the modified neurotoxin; the modified neurotoxin is botulinum type E comprising a leucine-based motif. The particular toxin dose and site of injection, as well as the frequency of toxin administrations, depend upon a variety of factors within the skill of the treating physician, as previously set forth. Within about 1 to about 7 days after the modified neurotoxin administration, the patient's pain is substantially reduced. The pain alleviation persists for up to 27 months.

Example 3

Peripheral Administration of a Modified Neurotoxin to Treat "Shoulder-Hand Syndrome"

Pain in the shoulder, arm, and hand can develop, with muscular dystrophy, osteoporosis and fixation of joints. While most common after coronary insufficiency, this syndrome can occur with cervical osteoarthritis or localized shoulder disease, or after any prolonged illness that requires the patient to remain in bed.

A 46 year old woman presents a shoulder-hand syndrome type pain. The pain is particularly localized at the deltoid region. The patient is treated by a bolus injection of a modified neurotoxin subcutaneously to the shoulder; preferably the modified neurotoxin is botulinum type E comprising a leucine-based motif. The modified neurotoxin can also be, for example, modified botulinum type A, B, C1, C2, D, E, F or G which comprise a leucine-based motif. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 4

Peripheral Administration of a Modified Neurotoxin to Treat Postherapeutic Neuralgia Postherapeutic neuralgia is one of the most intractable of chronic pain problems. Patients suffering this excruciatingly painful process often are elderly, have debilitating disease, and are not suitable for major interventional procedures. The diagnosis is readily made by the appearance of the healed lesions of herpes and by the patient's history. The pain is intense and emotionally distressing. Postherapeutic neuralgia can occur anywhere, but is most often in the thorax.

A 76 year old man presents a postherapeutic type pain. The pain is localized to the abdomen region. The patient is treated by a bolus injection of a modified neurotoxin intradermally to the abdomen; the modified neurotoxin is, for example, botulinum type A, B, C1, C2, D, E, F and/or G. The modified neurotoxin comprises a leucine-based motif and/or additional tyrosine-based motifs. The particular dose as well as the frequency of administration depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 5

Peripheral Administration of a Modified Neurotoxin to Treat Nasopharyngeal Tumor Pain These tumors, most often squamous cell carcinomas, are usually in the fossa of Rosenmuller and can invade the base of the skull. Pain in the face is common. It is constant, dull-aching in nature.

A 35 year old man presents a nasopharyngeal tumor type pain. Pain is found at the lower left cheek. The patient is treated by a bolus injection of a modified neurotoxin intramuscularly to the cheek, preferably the modified neurotoxin is botulinum type A, B, C1, C2, D, E, F or G comprising additional biological persistence enhancing amino acid derivatives, for example, tyrosine phosphorylations. The particular dose as well as the frequency of administrations depends upon a variety of factors within the skill of the treating physician. Within 1-7 days after modified neurotoxin administration the patient's pain is substantially alleviated. The duration of the pain alleviation is from about 7 to about 27 months.

Example 6

Peripheral Administration of a Modified Neurotoxin to Treat Inflammatory Pain A patient, age 45, presents an inflammatory pain in the chest region. The patient is treated by a bolus injection of a modified neurotoxin intramuscularly to the chest, preferably the modified neurotoxin is botulinum type A, B, C1, C2, D, E, F or G comprising additional tyrosine-based motifs. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 7

Treatment of Excessive Sweating

A male, age 65, with excessive unilateral sweating is treated by administering a modified neurotoxin. The dose and frequency of administration depends upon degree of desired effect. Preferably, the modified neurotoxin is botulinum type A, B, C1, C2, D, E, F and/or G. The modified neurotoxins comprise a leucine-based motif. The administration is to the gland nerve plexus, ganglion, spinal cord or central nervous system. The specific site of administration is to be determined by the physician's knowledge of the anatomy and physiology of the target glands and secretory cells. In addition, the appropriate spinal cord level or brain area can be injected with the toxin. The cessation of excessive sweating after the modified neurotoxin treatment is up to 27 months.

Example 8

Post Surgical Treatments

A female, age 22, presents a torn shoulder tendon and undergoes orthopedic surgery to repair the tendon. After the surgery, the patient is administered intramuscularly with a modified neurotoxin to the shoulder. The modified neurotoxin can botulinum type A, B, C, D, E, F, and/or G wherein one or more amino acids of a biological persistence enhancing component are deleted from the toxin. For example, one or more leucine residues can be deleted from and/or mutated from the leucine-based motif in botulinum toxin serotype A. Alternatively, one or more amino acids of the leucine-based motif can be substituted for other amino acids. For example, the two leucines in the leucine-based motif can be substituted for alanines. The particular dose as well as the frequency of administrations depends upon a variety of factors within the skill of the treating physician. The specific site of administration is to be determined by the physician's knowledge of the anatomy and physiology of the muscles. The administered modified neurotoxin reduces movement of the arm to facilitate the recovery from the surgery. The effect of the modified neurotoxin is for about five weeks or less.

Example 9

Cloning, Expression and Purification of the Botulinum Neurotoxin Light Chain Gene This example describes methods to clone and express a DNA nucleotide sequence encoding a botulinum toxin light chain and purify the resulting protein product. A DNA sequence encoding the botulinum toxin light chain can be amplified by PCR protocols which employ synthetic oligonucleotides having sequences corresponding to the 5' and 3' end regions of the light chain gene. Design of the primers can allow for the introduction of restriction sites, for example, Stu I and EcoR I restriction sites into the 5' and 3' ends of the botulinum toxin light chain gene PCR product. These restriction sites can be subsequently used to facilitate unidirectional subcloning of the amplification products. Additionally, these primers can introduce a stop codon at the C-terminus of the light chain coding sequence. Chromosomal DNA from *C. botulinum*, for example, strain HallA, can serve as a template in the amplification reaction.

The PCR amplification can be performed in a 0.1 mL volume containing 10 mM Tris-HCl (pH 8.3), 50 mM KCl, 1.5 mM MgCl2, 0.2 mM of each deoxynucleotide triphosphate (dNTP), 50 pmol of each primer, 200 ng of genomic DNA and 2.5 units of Taq DNA polymerase. The reaction mixture can be subjected to 35 cycles of denaturation (1 minute at 94° C.), annealing (2 minutes at 55° C.) and polymerization (2 minutes at 72° C.). Finally, the reaction can be extended for an additional 5 minutes at 72° C.

The PCR amplification product can be digested with for example, Stu I and EcoR I, to release the light chain encoding, cloned, PCR DNA fragment. This fragment can then be purified by, for example, agarose gel electrophoresis, and ligated into, for example, a Sma I and EcoR I digested pBluescript II SK phagemid. Bacterial transformants, for example, E. coli, harboring this recombinant phagemid can be identified by standard procedures, such as blue/white screening. Clones comprising the light chain encoding DNA can be identified by DNA sequence analysis performed by standard methods. The cloned sequences can be confirmed by comparing the cloned sequences to published sequences for botulinum light chains, for example, Binz, et al., in J. Biol. Chem. 265, 9153 (1990), Thompson et al., in Eur. J. Biochem. 189, 73 (1990) and Minton, Clostridial Neurotoxins, The Molecular Pathogenesis of Tetanus and Botulism p. 161-191, Edited by C. Motecucco (1995).

The light chain can be subcloned into an expression vector, for example, pMal-P2. pMal-P2 harbors the malE gene encoding MBP (maltose binding protein) which is controlled by a strongly inducible promoter, $P_{tac}$.

To verify expression of the botulinum toxin light chain, a well isolated bacterial colony harboring the light chain gene containing pMal-P2 can be used to inoculate L-broth containing 0.1 mg/ml ampicillin and 2% (w/v) glucose, and grown overnight with shaking at 30° C. The overnight cultures can be diluted 1:10 into fresh L-broth containing 0.1 mg/ml of ampicillin and incubated for 2 hours. Fusion protein expression can be induced by addition of IPTG to a final concentration of 0.1 mM. After an additional 4 hour incubation at 30° C., bacteria can be collected by centrifugation at 6,000×g for 10 minutes.

A small-scale SDS-PAGE analysis can confirm the presence of a 90 kDa protein band in samples derived from IPTG-induced bacteria. This MW would be consistent with the predicted size of a fusion protein having MBP (~40 kDa) and botulinum toxin light chain (~50 kDa) components.

The presence of the desired fusion proteins in IPTG-induced bacterial extracts can be confirmed by western blotting using the polyclonal anti-L chain probe described by Cenci di Bello et al., in Eur. J. Biochem. 219, 161 (1993). Reactive bands on PVDF membranes (Pharmacia; Milton Keynes, UK) can be visualized using an anti-rabbit immunoglobulin conjugated to horseradish peroxidase (BioRad; Hemel Hempstead, UK) and the ECL detection system (Amersham, UK). Western blotting results typically confirm the presence of the dominant fusion protein together with several faint bands corresponding to proteins of lower MW than the fully sized fusion protein. This observation suggests that limited degradation of the fusion protein occurred in the bacteria or during the isolation procedure.

To produce the subcloned light chain, pellets from 1 liter cultures of bacteria expressing the wild-type Botulinum neurotoxin light chain proteins can be resuspended in column buffer [10 mM Tris-HCl (pH 8.0), 200 mM NaCl, 1 mM EGTA and 1 mM DTT] containing 1 mM phenylmethanesulfonyl fluoride (PMSF) and 10 mM benzamidine, and lysed by sonication. The lysates can be cleared by centrifugation at 15,000×g for 15 minutes at 4° C. Supernatants can be applied to an amylose affinity column [2×10 cm, 30 ml resin] (New England BioLabs; Hitchin, UK). Unbound proteins can be washed from the resin with column buffer until the eluate is free of protein as judged by a stable absorbance reading at 280 nm. The bound MBP-L chain fusion protein can be subsequently eluted with column buffer containing 10 mM maltose. Fractions containing the fusion protein can be pooled and dialyzed against 20 mM Tris-HCl (pH 8.0) supplemented with 150 mM NaCl, 2 mM, CaCl2 and 1 mM DTT for 72 hours at 4° C.

The MBP-L chain fusion proteins can be purified after release from the host bacteria. Release from the bacteria can be accomplished by enzymatically degrading or mechanically disrupting the bacterial cell membrane. Amylose affinity chromatography can be used for purification. Recombinant wild-type or mutant light chains can be separated from the sugar binding domains of the fusion proteins by site-specific cleavage with Factor Xa. This cleavage procedure typically yields free MBP, free light chains and a small amount of uncleaved fusion protein. While the resulting light chains present in such mixtures can be shown to possess the desired activities, an additional purification step can be employed. For example, the mixture of cleavage products can be applied to a second amylose affinity column which binds both the MBP and uncleaved fusion protein. Free light chains can be isolated in the flow through fraction.

Example 10

Reconstitution of Native Light Chain, Recombinant Wild-Type Light Chain with Purified Heavy Chain Native heavy and light chains can be dissociated from a BoNT with 2 M urea, reduced with 100 mM DTT and then purified according to established chromatographic procedures. For example, Kozaki et al. (1981, Japan J. Med. Sci. Biol. 34, 61) and Maisey et al. (1988, Eur. J. Biochem. 177, 683). A purified heavy chain can be combined with an equimolar amount of either native light chain or a recombinant light chain. Reconstitution can be carried out by dialyzing the samples against a buffer consisting of 25 mM Tris (pH 8.0), 50 µM zinc acetate and 150 mM NaCl over 4 days at 4° C. Following dialysis, the association of the recombinant light chain and native heavy chain to form disulfide linked 150 kDa dichains is monitored by SDS-PAGE and/or quantified by densitometric scanning.

Example 11

Production of a Modified Neurotoxin with an Enhanced Biological Persistence

A modified neurotoxin can be produced by employing recombinant techniques in conjunction with conventional chemical techniques.

A neurotoxin chain, for example a botulinum light chain that is to be fused with a biological persistence enhancing component to form a modified neurotoxin can be produced recombinantly and purified as described in example 9.

The recombinant neurotoxin chain derived from the recombinant techniques can be covalently fused with (or coupled to) a biological persistence enhancing component, for example a leucine-based motif, a tyrosine-based motif and/or an amino acid derivative. Peptide sequences comprising biological persistence enhancing components can be synthesized by standard t-Boc/Fmoc technologies in solution or solid phase as is known to those skilled in the art. Similar synthesis techniques are also covered by the scope of this invention, for example, methodologies employed in Milton et al. (1992, *Biochemistry* 31, 8799-8809) and Swain et al. (1993, *Peptide Research* 6, 147-154). One or more synthesized biological persistence enhancing components can be fused to the light chain of botulinum type A, B, C1, C2, D, E, F or G at, for example, the carboxyl terminal end of the toxin. The fusion of the biological persistence enhancing components is achieved by chemical coupling using reagents and techniques known to those skilled in the art, for example PDPH/EDAC and Traut's reagent chemistry.

Alternatively, a modified neurotoxin can be produced recombinantly without the step of fusing the biological persistence enhancing component to a recombinant botulinum toxin chain. For example, a recombinant neurotoxin chain, for example, a botulinum light chain, derived from the recombinant techniques of example 9 can be produced with a biological persistence enhancing component, for example a leucine-based motif, a tyrosine-based motif and/or an amino acid derivative. For example, one or more DNA sequences encoding biological persistence enhancing components can be added to the DNA sequence encoding the light chain of botulinum type A, B, C1, C2, D, E, F or G. This addition can be done by any number of methods used for site directed mutagenesis which are familiar to those skilled in the art.

The recombinant modified light chain containing the fused or added biological persistence enhancing component can be reconstituted with a heavy chain of a neurotoxin by the method described in example 10 thereby producing a complete modified neurotoxin.

The modified neurotoxins produced according to this example have an enhanced biological persistence. Preferably, the biological persistence is enhanced by about 20% to about 300% relative to an identical neurotoxin without the additional biological persistence enhancing component(s).

Example 12

Production of a Modified Neurotoxin with a Reduced Biological Persistence

A modified neurotoxin with a reduced biological persistence can be produced by employing recombinant techniques. For example, a botulinum light chain derived from the recombinant techniques of example 9 can be produced without a biological persistence enhancing component. For example, one or more leucine-based motifs, tyrosine-based motifs and/or amino acid derivatives can be mutated. For example, one or more DNA sequences encoding biological persistence enhancing components can be removed from the DNA sequence encoding the light chain of botulinum type A, B, C1, C2, D, E, F or G. For example, the DNA sequence encoding the leucine based motif can be removed from the DNA sequence encoding botulinum type A light chain. Removal of the DNA sequences can be done by any number of methods familiar to those skilled in the art.

The recombinant modified light chain with the deleted biological persistence enhancing component can be reconstituted with a heavy chain of a neurotoxin by the method described in example 10 thereby producing a complete modified neurotoxin.

The modified neurotoxin produced according to this example has a reduced biological persistence. Preferably, the biological persistence is reduced by about 20% to about 300% relative to an identical neurotoxin, for example botulinum type A, with the leucine-based motif.

Although the present invention has been described in detail with regard to certain preferred methods, other embodiments, versions, and modifications within the scope of the present invention are possible. For example, a wide variety of modified neurotoxins can be effectively used in the methods of the present invention in place of Clostridial neurotoxins. Also, the corresponding genetic codes, i.e. DNA sequence, to the modified neurotoxins are also considered to be part of this invention. Additionally, the present invention includes peripheral administration methods wherein two or more modified neurotoxins, for example botulinum type E with a fused leucine-based motif and botulinum type B comprising a leucine-based motif, are administered concurrently or consecutively. While this invention has been described with respect to various specific examples and embodiments, it is to be understood that the invention is not limited thereto and that it can be variously practiced with the scope of the following claims.

Example 13

Production of a Modified Neurotoxin with a Reduced Biological Persistence

Localization to the cellular membrane is likely a key factor in determining the biological persistence of botulinum toxins. This is because localization to a cell membrane can protect the localized protein from inter-cellular protein degrading complexes.

It is well known and generally accepted that the biological persistence of botulinum type B neurotoxin is shorter than the biological persistence of botulinum type A neurotoxin. In this work, it was demonstrated that when the botulinum toxin type A light chain is truncated, which comprises removing the leucine-based motif, the light chain substantially loses its ability to localize to the cellular membrane in its characteristic pattern. In fact, truncated type A light chain localizes to the cellular membrane in a pattern similar to that of botulinum toxin type B light chain.

Therefore, it can be hypothesized that truncated botulinum type A has a reduced biological persistence and/or a reduced biological activity similar to that of botulinum toxin type B.

Example 14

Production of a Modified Neurotoxin with an Altered Biological Persistence

Localization to the cellular membrane is likely a key factor in determining the biological persistence of botulinum toxins. This is because localization to a cell membrane can protect the localized protein from inter-cellular protein degrading complexes.

In this work, it was demonstrated that when the botulinum toxin type A light chain is mutated, changing the two leucines at positions 427 and 428 to alanines (FIG. 3), the light chain substantially loses its ability to localize to the cellular membrane in its characteristic pattern.

From this data it can be concluded that the mutated botulinum type A has an altered biological persistence.

Example 15

In Vitro Cleavage of SNAP 25 by Truncated LC/A

Figure 9:
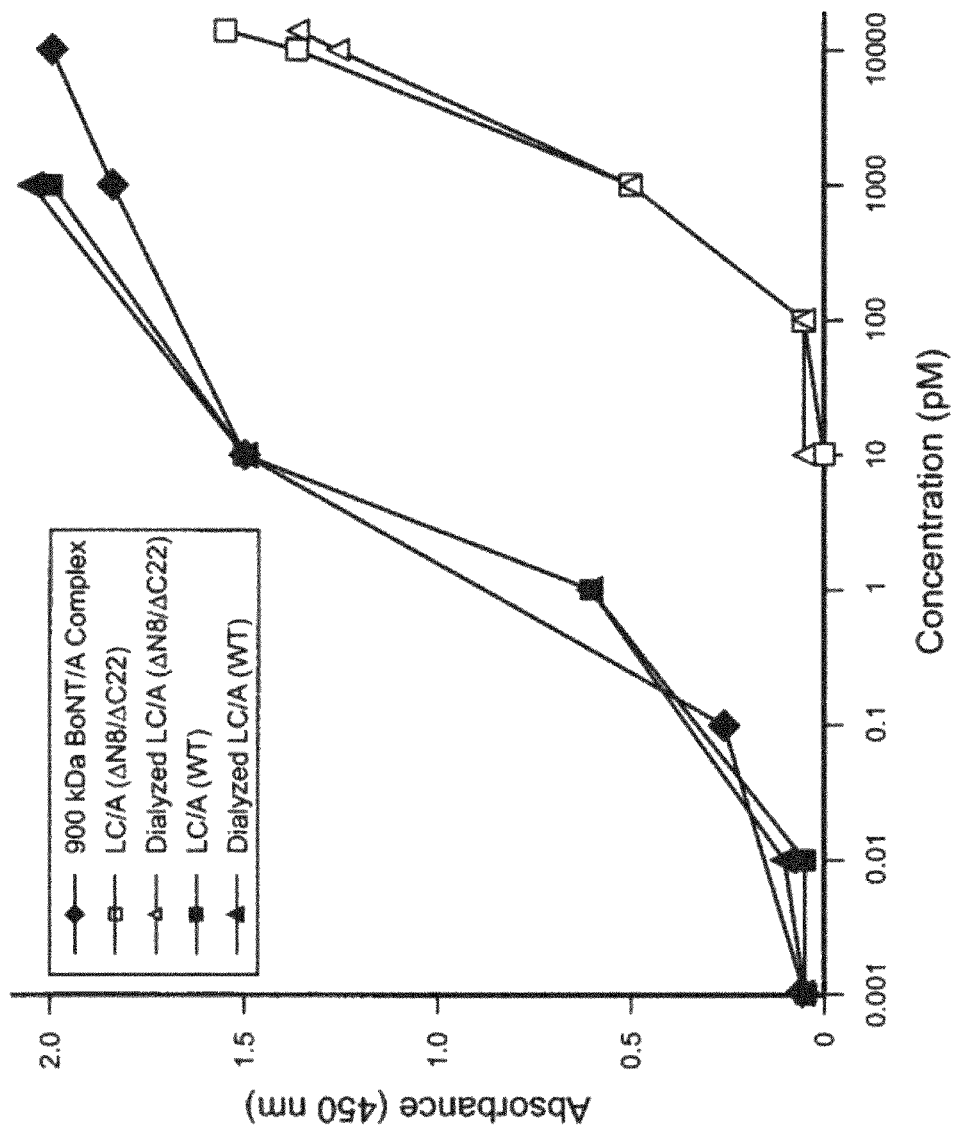
FIG. 9 is a graph which illustrates the results of an in vitro ELISA assay carried out by the inventors demonstrating that a truncated LC/A in vitro cleaves substrate at a slower rate or less efficiently than does non-truncated LC/A.

As illustrated by FIG. 9, an in vitro ELISA assay was carried out by the inventors demonstrating that a truncated LC/A in vitro cleaves SNAP-25 substrate less efficiently than does non-truncated LC/A. The data displayed is not a measure of inhibition of exocytosis but a measure of the in vitro formation of SNAP-25 cleavage. The assay was carried out as follows:

Materials:

BirA-SNAP25$_{128-206}$—this is a recombinant substrate for LC/A, consisting of a BirA signal sequence fused to the N-terminus of residues 128-206 of SNAP25. This fusion construct was produced in *E. coli* and the BirA signal sequence was biotinylated by the *E. coli*. Microtiter plates were coated with streptavidin. The toxin used was BoNT/A complex or LC/A constructs. The primary antibody was anti-SNAP25$_{197}$ antibody. This antibody recognizes the C-terminus of SNAP25 following cleavage by Type A toxin (BirA-SNAP25$_{128-197}$). The secondary antibody was goat, anti-rabbit IgG conjugated to horseradish peroxidase. The ImmunoPure TMB substrate was from Pierce, a colorimetric substrate for horseradish peroxidase. The antibody that recognizes the cleaved product SNAP25$_{197}$ is specific for that cleaved product and does not recognize the full length uncleaved substrate SNAP25$_{206}$.

Method:

BirA-SNAP25$_{128-206}$ was bound to streptavidin on a microtiter plate. To the plates were added serial dilutions of BoNT/A 900 kDa complex, His6-S-nativeLC/A, or His6-S-truncLC/A-His6. All toxin samples were pre-incubated with DTT (this is not required for the LC/A constructs, but they were treated the same as the BoNT/A complex). The toxin samples were incubated with the substrate for 90 minutes at 37° C. The toxin was removed and the bound substrate was incubated with anti-SNAP25$_{197}$ antibody. Unbound antibody was washed away and the plates were then incubated with the secondary antibody (anti-rabbit IgG conjugated to horseradish peroxidase). Unbound antibody was again washed away and a colorimetric assay for horseradish peroxidase was performed. The assay was quantified by reading the absorbance at 450 nm.

In other work by the inventors disclosed herein the light chain constructs that were expressed in the PC-12 cells were expressed directly in the PC-12 cells and do not contain any tags. The light chain constructs that have been expressed from *E. coli* for these in vitro assays contain affinity tags for purification purposes (these tags are not present on the proteins expressed in the PC-12 cells, as disclosed herein). The LC/A expressed in PC12 was the fusion protein GFP-LC/A. Between the GFP and the LC/A there is a set of Gly to separate both proteins.

An Explanation of the Various Constructs Follows:

Complex (red in the graph) this is BoNT/A 900 kDa complex isolated from *C. botulinum*

Truncated LC/A—construct lacking 8 amino acids at the N-terminus and 22 amino acids at the C-terminus. However, this construct does contain a 6-histidine and an S-tag at the N-terminus as well as a 6-histidine tag at the C-terminus.

Dialyzed Truncated LC/A—same as Truncated LC/A, but imidazole resulting from the purification has been removed.

Full LC/A (Dark green in graph)—native LC/A construct (full-length), but containing the N-terminal 6-histidine and S-tag. Does not have the C-terminal 6-histidine.

Dialyzed Full LC/A (Light green in graph)—Same as Full LC/A, but imidazole resulting from the purification has been removed.

Figure 10:
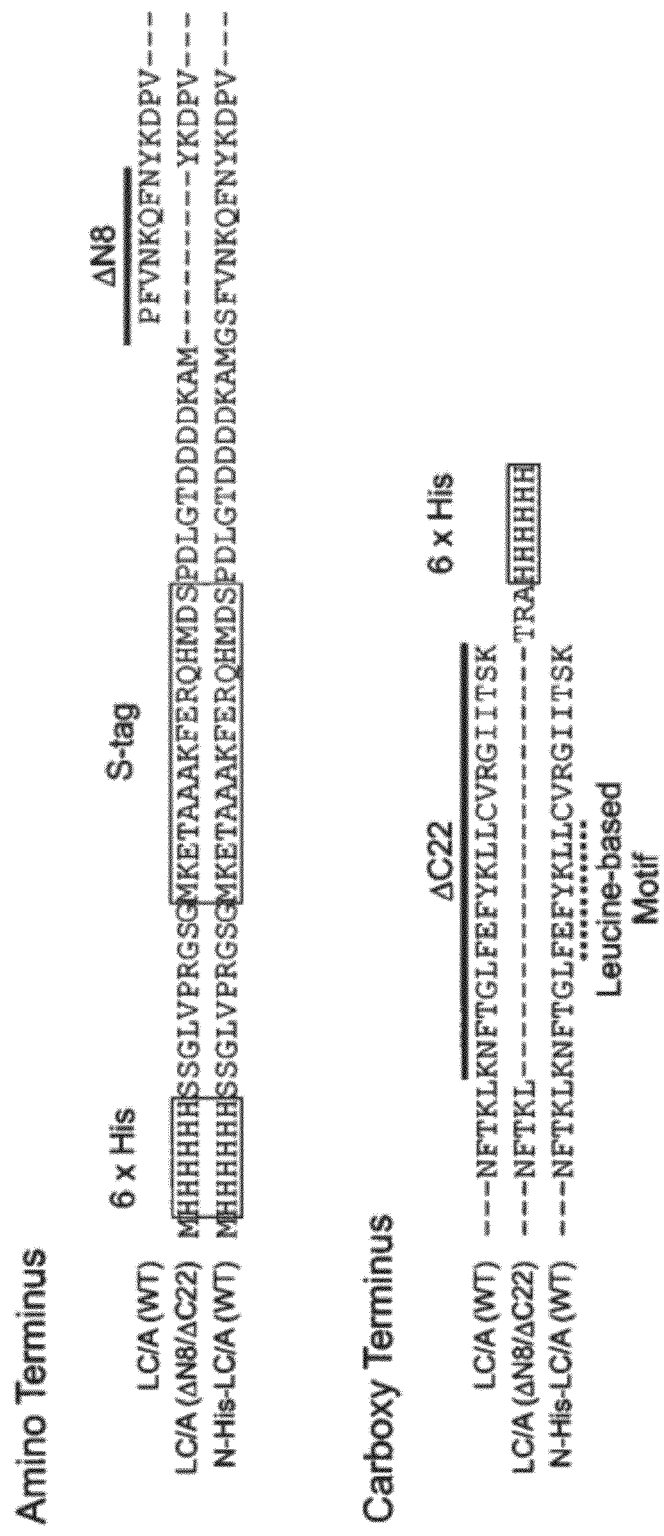
FIG. 10 shows a comparison of LC/A constructs expressed from *E. coli* for in vitro analysis. Alignment of the amino terminal end of the LC/A constructs compares the amino terminal end of the LC/A (WT) construct (SEQ ID NO: 36), the amino terminal end of the LC/A (ΔN8/ΔC22) construct (SEQ ID NO: 37), and the amino terminal end of the N-His-LC/A (WT) construct (SEQ ID NO: 38). Alignment of the carboxyl terminal end of the LC/A constructs compares the carboxyl terminal end of the LC/A (WT) construct (SEQ ID NO: 54), the carboxyl terminal end of the LC/A (ΔN8/ΔC22) construct (SEQ ID NO: 55), and the carboxyl terminal end of the N-His-LC/A (WT) construct (SEQ ID NO: 54).

To graphically depict these differences, FIG. 10 shows the very N-terminus and the very C-terminus of these constructs (the middle portion of the LC/A proteins is not shown). What is referred to as Wildtype corresponds to the native LC/A that the inventors had expressed directly in the PC-12 cells (this is construct that the inventors demonstrated activity with via Western blot analysis of the cleaved SNAP25 product). Truncated LC/A is the truncated light chain containing the His and S-tags. N-His-LC/A is what was referred to as Full LC/A in FIG. 9.

What is claimed is:

1. A modified *Clostridial botulinum* neurotoxin Type E having increased biological half-life consisting of one or more additional tyrosine-based motifs and one or more additional leucine-based motifs, wherein the tyrosine-based motif is SEQ ID NO: 24 or SEQ ID NO: 33, and wherein the leucine-based motif is SEQ ID NO: 15, SEQ ID NO: 18, SEQ ID NO: 19, or SEQ ID NO: 20,
    wherein the additional tyrosine-based motifs and additional leucine-based motifs increase biological half-life of the modified botulinum neurotoxin type E relative to an identical botulinum neurotoxin type E without the additional motifs.

2. A modified Clostridial neurotoxin Type E having increased biological half-life consisting of one or more additional tyrosine-based motifs and one or more additional leucine-based motifs, wherein the tyrosine-based motif is SEQ ID NO: 24 or SEQ ID NO: 33, and wherein the leucine-based motif is SEQ ID NO: 1, SEQ ID NO: 2, SEQ ID NO: 3, SEQ ID NO: 4, SEQ ID NO: 6, or SEQ ID NO: 13,
    wherein the additional tyrosine-based motifs and additional leucine-based motifs increase biological half-life of the modified botulinum neurotoxin type E relative to an identical botulinum neurotoxin type E without the additional motifs.

3. A composition comprising the modified Clostridial neurotoxin of claim 1.

4. A composition comprising the modified Clostridial neurotoxin of claim 2.

* * * * *

SEQUENCE LISTING

```
<160> NUMBER OF SEQ ID NOS: 55

<210> SEQ ID NO 1
<211> LENGTH: 7
<212> TYPE: PRT
<213> ORGANISM: Clostridial botulinum serotype A

<400> SEQUENCE: 1

Phe Glu Phe Tyr Lys Leu Leu
1               5

<210> SEQ ID NO 2
<211> LENGTH: 7
<212> TYPE: PRT
<213> ORGANISM: Rattus norvegicus

<400> SEQUENCE: 2

Glu Glu Lys Arg Ala Ile Leu
1               5

<210> SEQ ID NO 3
<211> LENGTH: 7
<212> TYPE: PRT
<213> ORGANISM: Rattus norvegicus

<400> SEQUENCE: 3

Glu Glu Lys Met Ala Ile Leu
```

<210> SEQ ID NO 4
<211> LENGTH: 7
<212> TYPE: PRT
<213> ORGANISM: Rattus norvegicus

<400> SEQUENCE: 4

Ser Glu Arg Asp Val Leu Leu
1               5

<210> SEQ ID NO 5
<211> LENGTH: 7
<212> TYPE: PRT
<213> ORGANISM: Rattus norvegicus

<400> SEQUENCE: 5

Val Asp Thr Gln Val Leu Leu
1               5

<210> SEQ ID NO 6
<211> LENGTH: 7
<212> TYPE: PRT
<213> ORGANISM: Mus musculus

<400> SEQUENCE: 6

Ala Glu Val Gln Ala Leu Leu
1               5

<210> SEQ ID NO 7
<211> LENGTH: 7
<212> TYPE: PRT
<213> ORGANISM: Xenopus laevis

<400> SEQUENCE: 7

Ser Asp Lys Gln Asn Leu Leu
1               5

<210> SEQ ID NO 8
<211> LENGTH: 7
<212> TYPE: PRT
<213> ORGANISM: Gallus gallus

<400> SEQUENCE: 8

Ser Asp Arg Gln Asn Leu Ile
1               5

<210> SEQ ID NO 9
<211> LENGTH: 7
<212> TYPE: PRT
<213> ORGANISM: Sheep

<400> SEQUENCE: 9

Ala Asp Thr Gln Val Leu Met
1               5

<210> SEQ ID NO 10
<211> LENGTH: 7
<212> TYPE: PRT
<213> ORGANISM: Homo sapiens

<400> SEQUENCE: 10

Ser Asp Lys Asn Thr Leu Leu
1               5

```
<210> SEQ ID NO 11
<211> LENGTH: 7
<212> TYPE: PRT
<213> ORGANISM: Homo sapiens

<400> SEQUENCE: 11

Ser Gln Ile Lys Arg Leu Leu
1               5

<210> SEQ ID NO 12
<211> LENGTH: 7
<212> TYPE: PRT
<213> ORGANISM: Homo sapiens

<400> SEQUENCE: 12

Ala Asp Thr Gln Ala Leu Leu
1               5

<210> SEQ ID NO 13
<211> LENGTH: 7
<212> TYPE: PRT
<213> ORGANISM: S. cerevisiae

<400> SEQUENCE: 13

Asn Glu Gln Ser Pro Leu Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Consensus sequence for Leucine-based motif.
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 14

Xaa Asp Xaa Xaa Xaa Leu Leu
1               5

<210> SEQ ID NO 15
<211> LENGTH: 7
<212> TYPE: PRT
<213> ORGANISM: Artificial Sequence
<220> FEATURE:
<223> OTHER INFORMATION: Consensus sequence for Leucine-based motif.
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 15

Xaa Glu Xaa Xaa Xaa Leu Leu
1               5

<210> SEQ ID NO 16
```

```
<211> LENGTH: 7
<212> TYPE: PRT
<213> ORGANISM: Artificial Sequence
<220> FEATURE:
<223> OTHER INFORMATION: Consensus sequence for Leucine-based motif.
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 16

Xaa Asp Xaa Xaa Xaa Leu Ile
 1               5

<210> SEQ ID NO 17
<211> LENGTH: 7
<212> TYPE: PRT
<213> ORGANISM: Artificial Sequence
<220> FEATURE:
<223> OTHER INFORMATION: Consensus sequence for Leucine-based motif.
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 17

Xaa Asp Xaa Xaa Xaa Leu Met
 1               5

<210> SEQ ID NO 18
<211> LENGTH: 7
<212> TYPE: PRT
<213> ORGANISM: Artificial Sequence
<220> FEATURE:
<223> OTHER INFORMATION: Consensus sequence for Leucine-based motif.
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 18

Xaa Glu Xaa Xaa Xaa Leu Ile
 1               5

<210> SEQ ID NO 19
<211> LENGTH: 7
<212> TYPE: PRT
<213> ORGANISM: Artificial Sequence
<220> FEATURE:
<223> OTHER INFORMATION: Consensus sequence for Leucine-based motif.
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
```

```
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 19

Xaa Glu Xaa Xaa Xaa Ile Leu
 1               5

<210> SEQ ID NO 20
<211> LENGTH: 7
<212> TYPE: PRT
<213> ORGANISM: Artificial Sequence
<220> FEATURE:
<223> OTHER INFORMATION: Consensus sequence for Leucine-based motif.
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 20

Xaa Glu Xaa Xaa Xaa Leu Met
 1               5

<210> SEQ ID NO 21
<211> LENGTH: 4
<212> TYPE: PRT
<213> ORGANISM: Artificial Sequence
<220> FEATURE:
<223> OTHER INFORMATION: Consensus sequence for Tyrosine-based motif.
<220> FEATURE:
<221> NAME/KEY: SITE
<222> LOCATION: (1)...(4)
<223> OTHER INFORMATION: Consensus sequence for Tyrosine-based motif.
<221> NAME/KEY: VARIANT
<222> LOCATION: (2)...(3)
<223> OTHER INFORMATION: Xaa is any amino acid.
<221> NAME/KEY: VARIANT
<222> LOCATION: (4)...(4)
<223> OTHER INFORMATION: Xaa is any hydrophobic amino acid.

<400> SEQUENCE: 21

Tyr Xaa Xaa Xaa
 1

<210> SEQ ID NO 22
<211> LENGTH: 4
<212> TYPE: PRT
<213> ORGANISM: Clostridial botulinum sertotype A

<400> SEQUENCE: 22

Lys Ala Phe Lys
 1

<210> SEQ ID NO 23
<211> LENGTH: 6
<212> TYPE: PRT
<213> ORGANISM: Clostridial botulinum sertotype A

<400> SEQUENCE: 23

Phe Asp Lys Leu Tyr Lys
 1               5

<210> SEQ ID NO 24
```

```
<211> LENGTH: 4
<212> TYPE: PRT
<213> ORGANISM: Clostridial botulinum serotype A

<400> SEQUENCE: 24

Tyr Lys Asp Pro
1

<210> SEQ ID NO 25
<211> LENGTH: 4
<212> TYPE: PRT
<213> ORGANISM: Clostridial botulinum serotype A

<400> SEQUENCE: 25

Tyr Ile Lys Ile
1

<210> SEQ ID NO 26
<211> LENGTH: 4
<212> TYPE: PRT
<213> ORGANISM: Clostridial botulinum serotype A

<400> SEQUENCE: 26

Tyr Asp Ser Thr
1

<210> SEQ ID NO 27
<211> LENGTH: 4
<212> TYPE: PRT
<213> ORGANISM: Clostridial botulinum serotype A

<400> SEQUENCE: 27

Tyr Gly Ser Thr
1

<210> SEQ ID NO 28
<211> LENGTH: 4
<212> TYPE: PRT
<213> ORGANISM: Clostridial botulinum serotype A

<400> SEQUENCE: 28

Tyr Asn Lys Phe
1

<210> SEQ ID NO 29
<211> LENGTH: 4
<212> TYPE: PRT
<213> ORGANISM: Clostridial botulinum serotype A

<400> SEQUENCE: 29

Tyr Met Lys Asn
1

<210> SEQ ID NO 30
<211> LENGTH: 4
<212> TYPE: PRT
<213> ORGANISM: Clostridial botulinum serotype A

<400> SEQUENCE: 30

Tyr Lys Met Leu
1

<210> SEQ ID NO 31
<211> LENGTH: 4
<212> TYPE: PRT
<213> ORGANISM: Clostridial botulinum serotype A
```

```
<400> SEQUENCE: 31

Tyr Leu Asn Phe
 1

<210> SEQ ID NO 32
<211> LENGTH: 4
<212> TYPE: PRT
<213> ORGANISM: Clostridial botulinum serotype A

<400> SEQUENCE: 32

Tyr Asp Gly Phe
 1

<210> SEQ ID NO 33
<211> LENGTH: 4
<212> TYPE: PRT
<213> ORGANISM: Clostridial botulinum serotype A

<400> SEQUENCE: 33

Tyr Lys Leu Leu
 1

<210> SEQ ID NO 34
<211> LENGTH: 437
<212> TYPE: PRT
<213> ORGANISM: Clostridial botulinum sertotype A

<400> SEQUENCE: 34

Pro Phe Val Asn Lys Gln Phe Asn Tyr Lys Asp Pro Val Asn Gly Val
 1               5                  10                  15

Asp Ile Ala Tyr Ile Lys Ile Pro Asn Ala Gly Gln Met Gln Pro Val
             20                  25                  30

Lys Ala Phe Lys Ile His Asn Lys Ile Trp Val Ile Pro Glu Arg Asp
         35                  40                  45

Thr Phe Thr Asn Pro Glu Glu Gly Asp Leu Asn Pro Pro Pro Glu Ala
     50                  55                  60

Lys Gln Val Pro Val Ser Tyr Tyr Asp Ser Thr Tyr Leu Ser Thr Asp
 65                  70                  75                  80

Asn Glu Lys Asp Asn Tyr Leu Lys Gly Val Thr Lys Leu Phe Glu Arg
                 85                  90                  95

Ile Tyr Ser Thr Asp Leu Gly Arg Met Leu Leu Thr Ser Ile Val Arg
            100                 105                 110

Gly Ile Pro Phe Trp Gly Gly Ser Thr Ile Asp Thr Glu Leu Lys Val
        115                 120                 125

Ile Asp Thr Asn Cys Ile Asn Val Ile Gln Pro Asp Gly Ser Tyr Arg
    130                 135                 140

Ser Glu Glu Leu Asn Leu Val Ile Ile Gly Pro Ser Ala Asp Ile Ile
145                 150                 155                 160

Gln Phe Glu Cys Lys Ser Phe Gly His Glu Val Leu Asn Leu Thr Arg
                165                 170                 175

Asn Gly Tyr Gly Ser Thr Gln Tyr Ile Arg Phe Ser Pro Asp Phe Thr
            180                 185                 190

Phe Gly Phe Glu Glu Ser Leu Glu Val Asp Thr Asn Pro Leu Leu Gly
        195                 200                 205

Ala Gly Lys Phe Ala Thr Asp Pro Ala Val Thr Leu Ala His Glu Leu
    210                 215                 220

Ile His Ala Gly His Arg Leu Tyr Gly Ile Ala Ile Asn Pro Asn Arg
225                 230                 235                 240
```

```
Val Phe Lys Val Asn Thr Asn Ala Tyr Tyr Glu Met Ser Gly Leu Glu
                245                 250                 255

Val Ser Phe Glu Glu Leu Arg Thr Phe Gly Gly His Asp Ala Lys Phe
            260                 265                 270

Ile Asp Ser Leu Gln Glu Asn Glu Phe Arg Leu Tyr Tyr Tyr Asn Lys
        275                 280                 285

Phe Lys Asp Ile Ala Ser Thr Leu Asn Lys Ala Lys Ser Ile Val Gly
    290                 295                 300

Thr Thr Ala Ser Leu Gln Tyr Met Lys Asn Val Phe Lys Glu Lys Tyr
305                 310                 315                 320

Leu Leu Ser Glu Asp Thr Ser Gly Lys Phe Ser Val Asp Lys Leu Lys
                325                 330                 335

Phe Asp Lys Leu Tyr Lys Met Leu Thr Glu Ile Tyr Thr Glu Asp Asn
            340                 345                 350

Phe Val Lys Phe Phe Lys Val Leu Asn Arg Lys Thr Tyr Leu Asn Phe
        355                 360                 365

Asp Lys Ala Val Phe Lys Ile Asn Ile Val Pro Lys Val Asn Tyr Thr
    370                 375                 380

Ile Tyr Asp Gly Phe Asn Leu Arg Asn Thr Asn Leu Ala Ala Asn Phe
385                 390                 395                 400

Asn Gly Gln Asn Thr Glu Ile Asn Asn Met Asn Phe Thr Lys Leu Lys
                405                 410                 415

Asn Phe Thr Gly Leu Phe Glu Phe Tyr Lys Leu Leu Cys Val Arg Gly
            420                 425                 430

Ile Ile Thr Ser Lys
            435

<210> SEQ ID NO 35
<211> LENGTH: 441
<212> TYPE: PRT
<213> ORGANISM: Clostridial botulinum sertotype B

<400> SEQUENCE: 35

Met Pro Val Thr Ile Asn Asn Phe Asn Tyr Asn Asp Pro Ile Asp Asn
  1               5                  10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175
```

```
Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
        210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
        290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
        370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys
        435                 440

<210> SEQ ID NO 36
<211> LENGTH: 13
<212> TYPE: PRT
<213> ORGANISM: Artificial Sequence
<220> FEATURE:
<223> OTHER INFORMATION: Amino terminus of the wild type BoNT/A light
      chain construct.
<220> FEATURE:
<221> NAME/KEY: PEPTIDE
<222> LOCATION: (1)...(13)
<223> OTHER INFORMATION: Amino terminus of the wild type BoNT/A light
      chain construct.

<400> SEQUENCE: 36

Pro Phe Val Asn Lys Gln Phe Asn Tyr Lys Asp Pro Val
1               5                   10

<210> SEQ ID NO 37
<211> LENGTH: 50
<212> TYPE: PRT
<213> ORGANISM: Artificial Sequence
<220> FEATURE:
<223> OTHER INFORMATION: Amino terminus of the LC/A (delN8/delC22)
      construct.
<220> FEATURE:
```

```
<221> NAME/KEY: PEPTIDE
<222> LOCATION: (1)...(50)
<223> OTHER INFORMATION: Amino terminus of the LC/A (delN8/delC22)
      construct.

<400> SEQUENCE: 37

Met His His His His His His Ser Ser Gly Leu Val Pro Arg Gly Ser
 1               5                  10                  15

Gly Met Lys Glu Thr Ala Ala Ala Lys Phe Glu Arg Gln His Met Asp
             20                  25                  30

Ser Pro Asp Leu Gly Thr Asp Asp Asp Lys Ala Met Tyr Lys Asp
         35                  40                  45

Pro Val
     50

<210> SEQ ID NO 38
<211> LENGTH: 59
<212> TYPE: PRT
<213> ORGANISM: Artificial Sequence
<220> FEATURE:
<223> OTHER INFORMATION: Amino terminus of the N-His-LC/A (WT)
      construct.
<220> FEATURE:
<221> NAME/KEY: PEPTIDE
<222> LOCATION: (1)...(47)
<223> OTHER INFORMATION: Amino terminus of the N-His-LC/A (WT)
      construct.

<400> SEQUENCE: 38

Met His His His His His His Ser Ser Gly Leu Val Pro Arg Gly Ser
 1               5                  10                  15

Gly Met Lys Glu Thr Ala Ala Ala Lys Phe Glu Arg Gln His Met Asp
             20                  25                  30

Ser Pro Asp Leu Gly Thr Asp Asp Asp Lys Ala Met Gly Ser Phe
         35                  40                  45

Val Asn Lys Gln Phe Asn Tyr Lys Asp Pro Val
     50                  55

<210> SEQ ID NO 39
<211> LENGTH: 447
<212> TYPE: PRT
<213> ORGANISM: Artificial Sequence
<220> FEATURE:
<223> OTHER INFORMATION: Consensus Sequence derived from BoNT/A light
      chain and BoNT/B light chain. Xaa means any amino acid.

<400> SEQUENCE: 39

Xaa Pro Xaa Xaa Xaa Xaa Asn Phe Asn Tyr Xaa Asp Pro Ile Xaa Xaa
 1               5                  10                  15

Xaa Xaa Ile Xaa Xaa Ile Xaa Xaa Pro Xaa Xaa Xaa Xaa Xaa Xaa Xaa
             20                  25                  30

Xaa Xaa Lys Ala Phe Lys Ile Xaa Xaa Lys Ile Trp Ile Ile Pro Glu
         35                  40                  45

Arg Xaa Thr Phe Xaa Xaa Xaa Xaa Glu Xaa Xaa Xaa Xaa Xaa Xaa Xaa
     50                  55                  60

Xaa Xaa Xaa Xaa Xaa Xaa Xaa Tyr Tyr Asp Xaa Xaa Tyr Leu Xaa
65                   70                  75                  80

Thr Xaa Xaa Xaa Lys Xaa Xaa Phe Leu Xaa Xaa Met Xaa Lys Leu Phe
             85                  90                  95

Xaa Arg Ile Xaa Ser Xaa Xaa Leu Gly Xaa Xaa Leu Leu Xaa Xaa Ile
         100                 105                 110

Ile Xaa Gly Ile Pro Phe Xaa Gly Xaa Xaa Xaa Ile Xaa Xaa Glu Xaa
```

```
                115                 120                 125
Xaa Xaa Xaa Xaa Xaa Xaa Xaa Ile Xaa Val Xaa Xaa Xaa Xaa Xaa
            130                 135                 140

Xaa Xaa Xaa Xaa Glu Xaa Xaa Xaa Xaa Xaa Xaa Asn Leu Ile Ile
145                 150                 155                 160

Xaa Gly Pro Xaa Xaa Xaa Ile Xaa Xaa Xaa Glu Xaa Xaa Xaa Gly
                165                 170                 175

Xaa Xaa Xaa Xaa Xaa Xaa Ser Arg Xaa Gly Phe Gly Xaa Xaa Xaa
            180                 185                 190

Ile Lys Phe Xaa Pro Asp Phe Xaa Xaa Phe Xaa Xaa Xaa Xaa Glu
                195                 200                 205

Xaa Xaa Xaa Xaa Xaa Ile Xaa Xaa Xaa Xaa Phe Xaa Ser Asp Pro
        210                 215                 220

Ala Leu Xaa Leu Xaa His Glu Leu Ile His Xaa Xaa His Xaa Leu Tyr
225                 230                 235                 240

Gly Ile Xaa Ile Xaa Xaa Xaa Xaa Xaa Xaa Xaa Asn Xaa Xaa Xaa
                245                 250                 255

Phe Phe Xaa Xaa Ser Xaa Xaa Xaa Ile Xaa Xaa Glu Glu Leu Xaa Thr
        260                 265                 270

Phe Gly Gly Xaa Asp Xaa Xaa Xaa Ile Xaa Xaa Xaa Xaa Asp Xaa Xaa
            275                 280                 285

Xaa Xaa Xaa Xaa Xaa Asn Xaa Phe Lys Xaa Ile Xaa Xaa Xaa Leu
290                 295                 300

Asn Lys Xaa Xaa Xaa Xaa Ile Xaa Xaa Xaa Xaa Xaa Ile Asn Xaa
305                 310                 315                 320

Xaa Lys Asn Xaa Lys Lys Asp Lys Tyr Xaa Xaa Xaa Glu Asp Ser Xaa
                325                 330                 335

Gly Lys Phe Ser Ile Asp Xaa Xaa Xaa Phe Asp Lys Leu Tyr Lys Xaa
                340                 345                 350

Leu Xaa Xaa Xaa Phe Thr Glu Xaa Asn Xaa Xaa Xaa Xaa Phe Lys Ile
        355                 360                 365

Xaa Xaa Arg Xaa Ser Tyr Xaa Xaa Xaa Xaa Xaa Xaa Xaa Lys Ile
        370                 375                 380

Xaa Xaa Ile Leu Xaa Xaa Xaa Xaa Tyr Thr Ile Xaa Asp Gly Phe Asn
385                 390                 395                 400

Ile Xaa Xaa Xaa Xaa Leu Xaa Xaa Xaa Phe Xaa Gly Gln Asn Xaa Xaa
                405                 410                 415

Ile Asn Xaa Xaa Xaa Phe Xaa Xaa Ile Xaa Xaa Xaa Xaa Xaa Xaa
                420                 425                 430

Xaa Xaa Tyr Lys Ile Xaa Xaa Xaa Lys Xaa Ile Xaa Xaa Xaa Xaa
            435                 440                 445

<210> SEQ ID NO 40
<211> LENGTH: 4
<212> TYPE: PRT
<213> ORGANISM: Artificial Sequence
<220> FEATURE:
<223> OTHER INFORMATION: Biological persistence altering component.

<400> SEQUENCE: 40

Asn Phe Asn Tyr
 1

<210> SEQ ID NO 41
<211> LENGTH: 5
<212> TYPE: PRT
<213> ORGANISM: Artificial Sequence
```

```
<220> FEATURE:
<223> OTHER INFORMATION: Biological persistence altering component.

<400> SEQUENCE: 41

Lys Ala Phe Lys Ile
 1               5

<210> SEQ ID NO 42
<211> LENGTH: 8
<212> TYPE: PRT
<213> ORGANISM: Artificial Sequence
<220> FEATURE:
<223> OTHER INFORMATION: Biological persistence altering component.

<400> SEQUENCE: 42

Lys Ile Trp Ile Ile Pro Glu Arg
 1               5

<210> SEQ ID NO 43
<211> LENGTH: 4
<212> TYPE: PRT
<213> ORGANISM: Artificial Sequence
<220> FEATURE:
<223> OTHER INFORMATION: Biological persistence altering component.

<400> SEQUENCE: 43

Gly Ile Pro Phe
 1

<210> SEQ ID NO 44
<211> LENGTH: 4
<212> TYPE: PRT
<213> ORGANISM: Artificial Sequence
<220> FEATURE:
<223> OTHER INFORMATION: Biological persistence altering component.

<400> SEQUENCE: 44

Asn Leu Ile Ile
 1

<210> SEQ ID NO 45
<211> LENGTH: 5
<212> TYPE: PRT
<213> ORGANISM: Artificial Sequence
<220> FEATURE:
<223> OTHER INFORMATION: Biological persistence altering component.

<400> SEQUENCE: 45

Ser Asp Pro Ala Leu
 1               5

<210> SEQ ID NO 46
<211> LENGTH: 5
<212> TYPE: PRT
<213> ORGANISM: Artificial Sequence
<220> FEATURE:
<223> OTHER INFORMATION: Biological persistence altering component.

<400> SEQUENCE: 46

His Glu Leu Ile His
 1               5

<210> SEQ ID NO 47
<211> LENGTH: 4
<212> TYPE: PRT
<213> ORGANISM: Artificial Sequence
<220> FEATURE:
<223> OTHER INFORMATION: Biological persistence altering component.
```

```
<400> SEQUENCE: 47

Leu Tyr Gly Ile
1

<210> SEQ ID NO 48
<211> LENGTH: 4
<212> TYPE: PRT
<213> ORGANISM: Artificial Sequence
<220> FEATURE:
<223> OTHER INFORMATION: Biological persistence altering component.

<400> SEQUENCE: 48

Thr Phe Gly Gly
1

<210> SEQ ID NO 49
<211> LENGTH: 5
<212> TYPE: PRT
<213> ORGANISM: Artificial Sequence
<220> FEATURE:
<223> OTHER INFORMATION: Biological persistence altering component.

<400> SEQUENCE: 49

Phe Lys Asp Lys Tyr
1               5

<210> SEQ ID NO 50
<211> LENGTH: 6
<212> TYPE: PRT
<213> ORGANISM: Artificial Sequence
<220> FEATURE:
<223> OTHER INFORMATION: Biological persistence altering component.

<400> SEQUENCE: 50

Gly Lys Phe Ser Ile Asp
1               5

<210> SEQ ID NO 51
<211> LENGTH: 5
<212> TYPE: PRT
<213> ORGANISM: Artificial Sequence
<220> FEATURE:
<223> OTHER INFORMATION: Biological persistence altering component.

<400> SEQUENCE: 51

Asp Gly Phe Asn Ile
1               5

<210> SEQ ID NO 52
<211> LENGTH: 4
<212> TYPE: PRT
<213> ORGANISM: Artificial Sequence
<220> FEATURE:
<223> OTHER INFORMATION: Biological persistence altering component.
      Xaa means any amino acid.

<400> SEQUENCE: 52

Tyr Leu Xaa Thr
1

<210> SEQ ID NO 53
<211> LENGTH: 4
<212> TYPE: PRT
<213> ORGANISM: Artificial Sequence
<220> FEATURE:
<223> OTHER INFORMATION: Biological persistence altering component.
```

-continued

```
<400> SEQUENCE: 53

Lys Ala Phe Lys
 1

<210> SEQ ID NO 54
<211> LENGTH: 27
<212> TYPE: PRT
<213> ORGANISM: Artificial Sequence
<220> FEATURE:
<223> OTHER INFORMATION: Carboxyl termini of the wild type BoNT/A
      light chain and the N-His-LC/A (WT) constructs.

<400> SEQUENCE: 54

Asn Phe Thr Lys Leu Lys Asn Phe Thr Gly Leu Phe Glu Phe Tyr Lys
 1               5                  10                  15

Leu Leu Cys Val Arg Gly Ile Ile Thr Ser Lys
            20                  25

<210> SEQ ID NO 55
<211> LENGTH: 14
<212> TYPE: PRT
<213> ORGANISM: Artificial Sequence
<220> FEATURE:
<223> OTHER INFORMATION: Carboxyl terminus of the LC/A (delN8/delC22)
      construct.

<400> SEQUENCE: 55

Asn Phe Thr Lys Leu Thr Arg Ala His His His His His His
 1               5                  10
```